(12) United States Patent
Stensrud et al.

(10) Patent No.: US 9,856,195 B2
(45) Date of Patent: Jan. 2, 2018

(54) PHOSPHONIC ACID CATALYST IN DEHYDRATIVE CYCLIZATION OF 5 AND 6 CARBON POLYOLS WITH IMPROVED COLOR AND PRODUCT ACCOUNTABILITY

(71) Applicant: Archer Daniels Midland Company, Decatur, IL (US)

(72) Inventors: Kenneth Stensrud, Decatur, IL (US); Alexandra Sanborn, Lincoln, IL (US); Stephen Howard, Sherman, IL (US); Erik Hagberg, Decatur, IL (US)

(73) Assignee: Archer-Daniels Midland Company, Decatur, IL (US)

( * ) Notice: Subject to any disclaimer, the term of this patent is extended or adjusted under 35 U.S.C. 154(b) by 0 days.

(21) Appl. No.: 15/302,400

(22) PCT Filed: Dec. 12, 2014

(86) PCT No.: PCT/US2014/070050
§ 371 (c)(1),
(2) Date: Oct. 6, 2016

(87) PCT Pub. No.: WO2015/156846
PCT Pub. Date: Oct. 15, 2015

(65) Prior Publication Data
US 2017/0029434 A1 Feb. 2, 2017

Related U.S. Application Data

(63) Continuation of application No. PCT/US2014/033580, filed on Apr. 10, 2014, and a continuation of application No. PCT/US2014/033581, filed on Apr. 10, 2014, and a continuation of application No. PCT/US2014/066298, filed on Nov. 19, 2014.

(51) Int. Cl.
| | |
|---|---|
| *C07C 29/76* | (2006.01) |
| *C07D 493/04* | (2006.01) |
| *B01J 27/053* | (2006.01) |
| *B01J 27/16* | (2006.01) |
| *B01J 31/02* | (2006.01) |
| *C07C 29/154* | (2006.01) |
| *B01D 1/22* | (2006.01) |
| *B01D 3/10* | (2006.01) |
| *B01D 15/18* | (2006.01) |
| *B01D 15/36* | (2006.01) |

(52) U.S. Cl.
CPC .............. *C07C 29/76* (2013.01); *B01D 1/22* (2013.01); *B01D 3/10* (2013.01); *B01D 15/1821* (2013.01); *B01D 15/361* (2013.01); *B01J 27/053* (2013.01); *B01J 27/16* (2013.01); *B01J 31/0225* (2013.01); *B01J 31/0227* (2013.01); *C07C 29/154* (2013.01); *C07D 493/04* (2013.01); *B01J 2231/4288* (2013.01); *B01J 2531/002* (2013.01); *B01J 2531/007* (2013.01)

(58) Field of Classification Search
CPC ... C07C 29/76; C07C 29/154; B01D 15/1821; B01D 15/361; B01D 3/10; B01D 1/22; B01J 27/053; B01J 31/0227; B01J 31/0225; B01J 27/16; B01J 2531/002; B01J 2531/007; B01J 2231/4288; C07D 493/04

See application file for complete search history.

(56) References Cited

U.S. PATENT DOCUMENTS

| | | | | | |
|---|---|---|---|---|---|
| 4,923,976 | A | * | 5/1990 | Arnaudis | ............... A61K 8/604 127/70 |
| 2013/0338381 | A1 | * | 12/2013 | Kim | ..................... C07D 493/04 549/464 |

OTHER PUBLICATIONS

Corma, A., "Lewis acids: from conventional homogeneous to green homogeneous and heterogeneous catalysis." Chemical Reviews 103.11 (2003): 4307-4366.*

* cited by examiner

*Primary Examiner* — John M Mauro
(74) *Attorney, Agent, or Firm* — William B. Miller

(57) ABSTRACT

A process for preparing cyclic dehydration products from sugar alcohols is described. The process involve using a mixed-acid catalyst reaction mixture containing a reducing acid, having a pKa of about 1.0-1.5, and at least a strong Brønsted acid or a Lewis acid, having a pKa≤0, or both acids in a solution to dehydrate and ring close said sugar alcohol. Synergistically, the mixed-acid catalysis can produce greater amounts of the desired product at similar levels of compositional accountability than either of the component acid catalysts acting alone.

8 Claims, 12 Drawing Sheets

PHOSPHONIC ACID CATALYST IN DEHYDRATIVE CYCLIZATION OF 5 AND 6 CARBON POLYOLS WITH IMPROVED COLOR AND PRODUCT ACCOUNTABILITY

BENEFIT OF PRIORITY

The present application is a national phase application of International Application No. PCT/US2014/070050, filed Dec. 12, 2014, which claims benefit of priority from International Application Nos. PCT/US2014/033580, and PCT/US2014/033581, both filed Apr. 10, 2014, and International Application No. PCT/US2014/066298, filed Nov. 19, 2014, the contents of each are incorporated herein by reference.

FIELD OF INVENTION

The present invention relates to certain bi-functional molecules and their preparation. In particular, the present invention pertains to a catalytic dehydration process of sugar alcohols to generate dianhydro-sugars.

BACKGROUND

Traditionally, polymers and commodity chemicals have been prepared from petroleum-derived feedstocks. However, as petroleum reservoirs are rapidly depleting and concomitantly becoming more difficult to access, an exigency to develop renewable or "green" alternative materials from biologically-derived resources has been at the vanguard of much current research, particularly in the role of commercially tenable surrogates to conventional, petroleum-based or -derived counterparts, or for generating the same materials as produced from fossil, non-renewable sources.

One of the most abundant kinds of biologically-derived or renewable alternative feedstock for such materials is carbohydrates. Carbohydrates, however, are generally unsuited to current high temperature industrial processes. In contrast to petroleum-based, hydrophobic aliphatic or aromatic feedstocks with a low degree of functionalization, carbohydrates such as sugars are complex, highly functionalized hydrophilic materials. As a consequence, researchers have sought to produce biologically-based chemicals that originate from carbohydrates, but which are less highly functionalized, including more stable bi-functional compounds, such as 2,5-furandicarboxylic acid (FDCA), levulinic acid, and 1,4:3,6-dianhydrohexitols.

1,4:3,6-dianhydrohexitols (also referred to herein as isohexides) are derived from renewable resources from cereal-based polysaccharides. Isohexides embody a class of bicyclic furanodiols that derive from the corresponding reduced sugar alcohols, namely D-sorbitol, D-mannitol, and D-iditol, respectively. Depending on chirality, the three isomers of the isohexides are: A) isosorbide, B) isomannide, and C) isoidide, respectively, the structures of which are illustrated in Scheme 1.

Scheme 1: Structures of isomannide A, isosorbide B, and isoidide C.

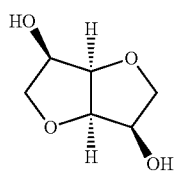

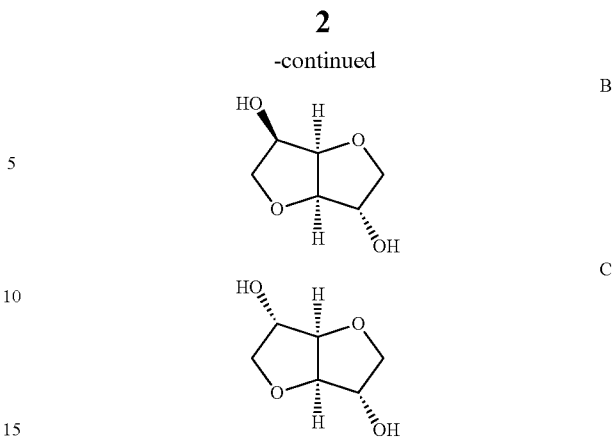

The conventional chemistry used for dehydration of sugar alcohols to produce dianhydrohexides generates undesired byproducts. The high cost and complexity of current methods for the separation of isohexides from the numerous byproducts makes the development of less expensive and simpler alternatives highly desirable. Hence, a process which can enhance greater conversion and higher yield of the desired product, as well as lessens amount of byproducts would be welcome.

SUMMARY OF THE INVENTION

The present disclosure describes, in part, a process for preparing a cyclic dehydration product. The process involves contacting a sugar alcohol with a mixed-acid catalyst reaction mixture containing a reducing Brønsted acid, having a pKa of about 1.0-1.5, in combination with at least a strong Brønsted acid or a Lewis acid, having a pKa≤0, or both kinds of strong Brønsted and Lewis acids in a solution at a temperature and for a time sufficient to dehydrate and ring close the sugar alcohol molecule to a corresponding cyclic dehydration product in a product mixture. The process can enable marked improvements in overall conversion rates and product yields, without significant deleterious effects on the level of product accountability, and reduced color body formation.

The ratio of reducing acid and at least a Brønsted acid or Lewis acid are present in relative amounts from about 1000:1 to about 5:1. The process can produce at least a 3% increase in relative yield of a dianhydro-sugar product relative to a dehydration reaction using either the reducing Brønsted acid, the strong Brønsted acid, or Lewis acid separately and alone under the same respective acid catalyst load for the same reaction time and temperature.

Additional features and advantages of the present processes will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Figure 1:
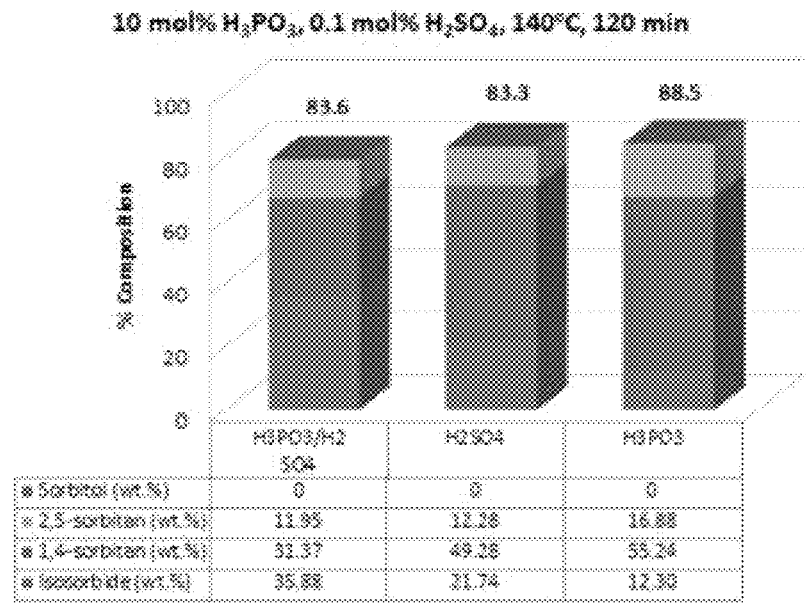
FIG. 1 is a bar graph showing the compositional accountability of the product mixture from three dehydration cyclization reactions of sorbitol catalyzed with 1) 10 mol. % $H_3PO_3$, alone, 2) 0.1 mol. % $H_2SO_4$, alone, and 3) combining the two in a mixed acid catalyst, at 140° C. for 2 h. (120 min.).

The present disclosure describes a process that can improve conversion and yields, and enhance compositional accountability in product mixtures prepared from dehydration reactions of sugar alcohols. In general, the process involves contacting a sugar alcohol with a mixed-acid catalyst containing a reducing Brønsted acid, having a pKa of about 1.0-1.5, and either a strong Brønsted acid or Lewis acid, having a pKa≤0, or both acids in a solution to dehydrate and ring close the sugar alcohol molecule to its corresponding cyclic dehydration product.

When a sugar alcohol is dehydrated by an acid catalyst some byproducts are typically formed. These undesired products and are not easily identifiable, meaning there are products formed that are not identified as a particular cyclic dehydration derivative species (e.g., an isohexide or sorbitan compound). These difficult to identify byproducts include polymeric condensates and color bodies, both of which impart an unwanted color and opacity to the reaction mixture. "Accountability" as used herein, is a measure of the percentage of the product mixture that can be quantitatively identified as cyclic dehydration derivative compounds and unreacted starting materials, but excludes poly-condensates, color bodies or other species (e.g., furanic compounds) that are not identified as a cyclic dehydration product.

The methods described herein are exemplified by use of phosphonic acid ($H_3PO_3$) also known as phosphorus acid as the reducing Brønsted acid, to perform the dehydration of sugar alcohols to their corresponding cyclic derivatives. According to an advantageous feature of the present methods, use of phosphonic acid in combination with other acids to dehydrate sugar alcohols results in a product mixture with high accountability relative to a dehydration reaction catalyzed with a single acid (e.g., sulfuric acid).

We discovered surprisingly that a combination of two or more acid catalysts has significant synergistic benefits as reflected in conversion yields of cyclic dehydration products (e.g., dianhydrosugar compounds) and compositional accountability results. In general, the mixed-acid catalysis can produce greater amounts of desired product at comparable levels of compositional accountability than either of the component acid catalysts acting alone. According to the process, the reaction leads to a product mixture having at least a 3%-5% increase in relative yield of a specific cyclic dehydration product relative to a dehydration reaction using either the reducing Brønsted acid, the strong Brønsted acid, or Lewis acid separately and alone under the same respective acid catalyst loads for the same reaction time and temperature. In certain embodiments, the relative yield of specific cyclic dehydration products relative to a dehydration reaction catalyzed with each of the acids singly or separately is increased by about 7% to about 20% or greater (e.g., about 10% or 11% to about 15% or 18% with optimization of reaction conditions). In certain favored embodiments, the yield from combined or multiple acid catalysis can be at least double or triple the amount yielded from catalysis using the individual single acids in the combined catalysis.

In the product mixtures of the combined acid catalysis one does not observe a significant build-up of color bodies, as attended by the product accountability, relative to the product mixtures from single acid catalysis (see e.g., Table 2.). The reaction can generate a product mixture that has a relative percentage of compositional accountability that is either a) equal to, b) greater than or c) not less than about 20% (typically, not less than 12% to about 18%) of a compositional accountability derived from a dehydration reaction using either the reducing acid, the strong Brønsted acid, or Lewis acid separately and alone. In certain embodiments, the product accountability of the synergistic combined acid catalysis is not less than about 2%-10% relative to that of a compositional accountability derived from a dehydration reaction using either the reducing acid, the strong Brønsted acid, or Lewis acid separately and alone under the same respective acid catalyst loads for the same reaction time and temperature. To illustrate, the compositional accountability value for each of the combined mixed-acid catalysis reactions in FIGS. 1 and 2 (respectively 83.6% and 82.8%) is about equal to the accountability value for each of the reactions catalyzed with sulfuric acid alone (respectively 83.3% and 82.6%), while also being slightly less than the value for each of the reaction using phosphonic acid alone (respectively 88.5% and 89.2%). Further, the compositional accountability value for each of the combined mixed-acid catalysis reactions in FIGS. 11 and 12 (respectively 94.0% and 95.1%) is greater than the accountability value for each of the reactions catalyzed by phosphonic acid alone (respectively 89.7% and 91.5%), while also being less than the accountability value for each of the reactions catalyzed by gallium triflate alone (respectively 99.9% and 100%).

The multiple or combined acid catalysis can be employed in the conversion of various different sugar alcohol species to their corresponding products. According to certain embodiments, the sugar alcohol can be, for example, sorbitol, mannitol, iditol, xylitol and erythritol. Alternatively, the reagent can be a dehydration product of sugar alcohols, such as 1,2,5,6-hexanetetrol (HTO). For instance, sorbitol is converted to isosorbide by means of intramolecular dehydrative cyclization of sorbitol to sorbitans, then isosorbide. In another example, xylitol can be dehydrated directly to 1,4-anhydroxylitol. Alternatively, HTO is cyclized dehydratively to racemic THF dimethanols.

The reducing Brønsted acid may be at a catalyst load of about 0.5 mol. % or 1 mol. % or 2 mol. % to about 15 mol. % or 20 mol. %, relative to the concentration of the sugar alcohol, or any combination of range values therein. In certain other embodiments, the phosphonic acid is at a catalyst load in a range from about 5 mol. % or 7 mol. % to about 10 mol. % or 13 mol. % In favored embodiments, the reducing Brønsted acid is phosphonic acid ($H_3PO_3$).

The strong Brønsted acid can be, for example, hydrochloric acid (HCl), sulfuric acid ($H_2SO_4$), p-toluenesulfonic acid (p-TsOH), methane sulfonic acid, or trifluoromethansulfonic acid.

The Lewis acid is water tolerant. That is, the Lewis acid is not deactivated in the presence of water. The Lewis acid may include at least one of: aluminum trifluoromethanesulfonate ($Al(OTf)_3$), gallium trifluoromethanesulfonate ($Ga(OTf)_3$), bismuth trifluormethanesulfonate ($Bi(OTf)_3$), scandium trifluoromethanesulfonate ($Sc(OTf)_3$), indium trifluoromethanesulfonate ($In(OTf)_3$), tin triflate ($Sn(OTf)_2$), and hafnium triflate ($Hf(OTf)_4$).

The strong Brønsted acid or Lewis acid each may have a catalyst load of about 0.005 mol. % or 0.1 mol. % to about 2 mol. % or about 5 mol. %, relative to the concentration of the sugar alcohol. In general, the amount of reducing Brønsted acid present is greater than either strong Brønsted acid or Lewis acid catalyst loadings. The amount of reducing Brønsted acid catalyst and either strong Brønsted acid or Lewis acid catalyst allotted in the combined acid catalysis is in a ratio from about 1000:1 to about 5:1, inclusive of various combination ranges therein between. Ideally, given the highly reactive nature of Lewis acids, the reducing Brønsted acid vs. Lewis acid loading is about 100:1 to 1000:1. Typically, the ratios can be about 250:1, 200:1, 150:1, or 100:1. For the present disclosure, the Lewis acid activity in descending order is: Hf>Ga>Sc>Bi>In>Al>Sn. Ideally, the reducing Brønsted acid vs. strong Brønsted acid loading is about 100:1 to 5:1. Typically, the ratios can be narrower, about 70:1, 50:1, 40:1 to about 20:1, 15:1, or 10:1.

The reaction time can be about 4 or 6 hours, but typically to minimize color body formation the reaction times are shorter, between about 1 hour to about 2.5 or 3 hours. (See e.g., Table 2.)

The reaction temperature may be in a range from about 100° C. up to about 180° C. or 190° C. Typically, the reaction temperature is in a range from about 110° C. to about 150° C. or 165° C.

To obtain optimal product yields, the dehydration reaction is performed under vacuum at an operating pressure of about 5 torr to about 100 torr. Typically, the operating pressure is between about 10 torr to about 30 torr, preferably between about 12 or 15 torr to about 20 or 25 torr.

1. Sugar Alcohol

While the advantageous features of the processes described herein are exemplified with sorbitol dehydration, the present processes can be employed for transforming various sugar alcohol or dehydration product compounds of sugar alcohols (e.g., sorbitol, mannitol, iditol, xylitol, erythritol, and 1,2,5,6-hexanetetrol (HTO)) in the preparation of their dehydration products.

For purpose of illustration, Table 1 summarizes the results of catalytic dehydration reactions of sorbitol under various reaction conditions according to embodiments of the present process. In Examples 1-21, the dehydration reactions use phosphonic acid ($H_3PO_3$), at several different catalyst loads that range from about 2.5 mol. % to about 10 mol. % in combination with some examples of strong Brønsted and Lewis acids, also at various catalyst loads. These reactions are performed at various temperatures between about 110° C. to about 150° C., over a period of about 1, 2, or 3 hours. As the results show, several examples of the phosphonic acid catalysis can produce relatively good rates of conversion of sorbitol to isosorbide without significant loss of composition accountability levels for the product mixture. The yield of isosorbide is either better than or comparable to reactions that use a strong Brønsted acid, such as sulfuric acid ($H_2SO_4$) as the catalyst. (See, Comparative Examples 1-7 in Table 3.) In certain examples, the combination of phosphonic acid catalyst with a strong, water-tolerant Lewis acid catalyst, such as bismuth triflate ($Bi(OTf)_3$), generates improved yields of isosorbide relative to the use of the Lewis acid alone.

Phosphonic acid exhibits an inherently reductive ability and antioxidant behavior. It is believed that the phosphonic acid functions both as a catalyst for dehydrative cyclization and as reducing agent to help mitigate color development in the product. From the examples and results in the accompanying figures, a favored range for operating conditions of the dehydrative reactions may include phosphonic acid with a concentration of about 2 mol % or 5 mol % to about 10 mol % or 20 mol %, depending on the reaction time and temperature. Longer durations and higher temperatures should be balanced for optimal reaction results.

The unique utility and significant performance characteristics of phosphonic acid as a catalyst can generate both good conversion rates and product accountabilities. Certain examples with different combinations of catalyst loads, temperature, and time exhibited particularly advantageous results. This suggests potential improvements in combined acid systems. The higher isosorbide yield in the samples highlight a beneficial impact of phosphonic acid with strong Brønsted and Lewis acids, in particular when present at higher acid concentrations.

In Example 1-4, the sulfuric acid catalysis of sorbitol yields about 20-24 wt. % of isosorbide, with about 80%-84% product accountability. The phosphonic acid catalysis of sorbitol produces about 5-20 wt. % of isosorbide, with about 85-85% product accountability. The combined acid catalysis generally produces about 1.3-2× greater amount of isosorbide (e.g., ~25-45 wt. %) than the dehydrative reactions using each of the single acid catalysts alone, with comparable levels of product accountability (e.g., ~80-87%).

These results compare favorably to similar results for the reactions in Examples 5-10, which present catalysis with p-toluenesulfonic acid, phosphonic acid, and combination of the two acids. Sorbitol catalyzed with p-TsOH alone yields about 5-9% of isosorbide, with about 89%-95% product accountability. The phosphonic acid catalysis of sorbitol produces about 2-18% of isosorbide, with about 85-98% product accountability. The combined acid catalysis generally produces about 2-6× greater amount of isosorbide (e.g., ~13-36 wt. %) than the dehydrative reactions using each of the single acid catalysts alone, with comparable levels of product accountability (e.g., ~80% or 82% to 94% or 95%).

Similarly, Examples 11-17 presents catalysis with gallium trifluoromethanesulfonate, phosphonic acid, and combination of the two acids. Sorbitol catalyzed with $Ga(OTf)_3$ alone yields minimal amounts of isosorbide (0-1 wt. %), with about 89%-95% product accountability. The phosphonic acid catalysis of sorbitol produces about 2-18% of isosorbide, with about 85-98% product accountability. The combined acid catalysis generally produces at least 2× or 3× greater amount of isosorbide (e.g., ~7-34 wt. %) than the dehydrative reactions using each of the single acid catalysts alone, with comparable levels of product accountability (e.g., ~80% or 82% to 94% or 95%).

Given the highly reactive nature of the Lewis acid, the amount of Lewis acid employed is kept at a low concentration, which results in lower conversion yields of isosorbide. In comparison, a change in the amount of acid used, as in Example 18, causes an increase in the reactivity by an order of magnitude to generate more isosorbide. In Example 18, sorbitol is catalyzed with a) aluminum trifluoromethanesulfonate, b) phosphonic acid, and a combination of the two acids (a & b) to isosorbide with yields of about 13.39 wt. %, 5.18 wt. %, and 40.07 wt. %, respectively. The product accountability is 89.0% for $Al(OTf)_3$, 94.1% for $H_3PO_3$, and 85.8% for the combined acids.

Examples 19 and 20 present catalysis using: bismuth trifluoromethanesulfonate, p-toluenesulfonic acid, phosphonic acid, and combination of the three component acids. Sorbitol catalyzed with $Bi(OTf)_3$ alone yields minimal amounts of isosorbide (0-1 wt. %), with about 97%-99% product accountability. The p-TsOH catalysis of sorbitol produces about 2-8 wt. % of isosorbide, with about 90-95% product accountability. The phosphonic acid catalysis of sorbitol produces about 2-6% of isosorbide, with about 93-96% product accountability. The combined multi-acid catalysis generally produces at least 2× or 4× greater amount of isosorbide (e.g., ~17-42 wt. %) than the dehydrative reactions using each of the single acid catalysts alone, with comparable levels of product accountability (e.g., ~85%-90%).

Example 21 summarizes catalysis using: hafnium trifluoromethanesulfonate, p-toluenesulfonic acid, phosphonic acid, and mixed combination of the three component acids. Sorbitol catalyzed with Hf(OTf)$_4$ alone yields about 6.62 wt. % of isosorbide, with about 96.6% product accountability. The p-TsOH catalysis of sorbitol produces about 2.36 wt. % of isosorbide, with about 93.7% product accountability. The phosphonic acid catalysis of sorbitol produces about 5.18% of isosorbide, with about 94.1% product accountability. The combined multi-acid catalysis produces at least about 3× or 5× up to about 12× greater amount of isosorbide (e.g., ~29.18 wt. %) than the dehydrative reactions using each of the single acid catalysts alone, with comparable levels of product accountability (e.g., ~86.3%).

TABLE 1

Summary of Co-catalysis Results

| Ex. | Catalysts | Catalyst Load (mol %) | Time (min) | Temp (° C.) | Sorbitol (wt. %) | Isosorbide (wt. %) | 1,4-sorbitan (wt. %) | 2,5-sorbitan(s) (wt. %) | Accountability (%) w/o Catalyst | Accountability (%) + Catalysts |
|---|---|---|---|---|---|---|---|---|---|---|
| 1 | H$_3$PO$_3$/H$_2$SO$_4$ | 10/0.1 | 120 | 140 | 0 | 35.88 | 31.37 | 11.95 | 79.2 | 83.6 |
|   | H$_2$SO$_4$ | 0.1 | 120 | 140 | 0 | 21.74 | 49.28 | 12.28 |  | 83.3 |
|   | H$_3$PO$_3$ | 10 | 120 | 140 | 0 | 12.30 | 55.24 | 16.88 |  | 88.5 |
| 2 | H$_3$PO$_3$/H$_2$SO$_4$ | 10/0.1 | 60 | 150 | 0 | 40.39 | 24.36 | 18.05 | 78.5 | 82.8 |
|   | H$_2$SO$_4$ | 0.1 | 60 | 150 | 0 | 23.82 | 47.95 | 10.87 |  | 82.6 |
|   | H$_3$PO$_3$ | 10 | 60 | 150 | 0 | 16.33 | 57.50 | 15.37 |  | 89.2 |
| 3 | H$_3$PO$_3$/H$_2$SO$_4$ | 5/0.1 | 120 | 140 | 0 | 33.81 | 35.32 | 14.77 | 83.9 | 86.2 |
|   | H$_2$SO$_4$ | 0.1 | 120 | 140 | 0 | 21.74 | 49.28 | 12.28 |  | 83.3 |
|   | H$_3$PO$_3$ | 5 | 120 | 140 | 20.8 | 9.76 | 52.10 | 7.05 |  | 89.7 |
| 4 | H$_3$PO$_3$/H$_2$SO$_4$ | 5/0.1 | 60 | 150 | 0 | 27.17 | 44.62 | 10.31 | 82.1 | 84.5 |
|   | H$_2$SO$_4$ | 0.1 | 60 | 150 | 0 | 23.82 | 47.95 | 10.87 |  | 82.6 |
|   | H$_3$PO$_3$ | 5 | 60 | 150 | 24.47 | 5.18 | 49.00 | 15.40 |  | 94.1 |
| 5 | H$_3$PO$_3$/pTsOH | 10/0.1 | 120 | 140 | 0 | 29.23 | 33.56 | 17.81 | 80.6 | 85.0 |
|   | pTsOH | 0.1 | 120 | 140 | 17 | 6.92 | 63.22 | 6.26 |  | 93.4 |
|   | H$_3$PO$_3$ | 10 | 120 | 140 | 0 | 12.30 | 55.24 | 16.88 |  | 88.5 |
| 6 | H$_3$PO$_3$/pTsOH | 10/0.1 | 60 | 150 | 0 | 32.43 | 32.11 | 15.96 | 80.5 | 84.9 |
|   | pTsOH | 0.1 | 60 | 150 | 12.6 | 7.13 | 59.24 | 12.71 |  | 91.7 |
|   | H$_3$PO$_3$ | 10 | 60 | 150 | 0.0 | 16.33 | 57.50 | 15.37 |  | 89.2 |
| 7 | H$_3$PO$_3$/pTsOH | 5/0.1 | 120 | 140 | 0 | 18.53 | 55.85 | 15.22 | 89.6 | 91.9 |
|   | pTsOH | 0.1 | 120 | 140 | 17 | 6.92 | 63.22 | 6.26 |  | 93.4 |
|   | H$_3$PO$_3$ | 5 | 120 | 140 | 20.8 | 9.76 | 52.10 | 7.05 |  | 89.7 |
| 8 | H$_3$PO$_3$/pTsOH | 5/0.1 | 60 | 150 | 0 | 14.12 | 53.51 | 16.37 | 84.0 | 87.0 |
|   | pTsOH | 0.1 | 60 | 150 | 13 | 7.13 | 59.24 | 12.31 |  | 91.7 |
|   | H$_3$PO$_3$ | 5 | 60 | 150 | 24.47 | 5.18 | 49.00 | 15.40 |  | 94.1 |
| 9 | H$_3$PO$_3$/pTsOH | 2.5/0.1 | 120 | 140 | 0 | 20.19 | 50.64 | 9.49 | 87.5 | 89.2 |
|   | pTsOH | 0.1 | 120 | 140 | 17 | 6.92 | 63.22 | 6.26 |  | 93.4 |
|   | H$_3$PO$_3$ | 2.5 | 120 | 140 | 43.5 | 2.23 | 40.28 | 10.71 |  | 96.7 |
| 10 | H$_3$PO$_3$/pTsOH | 2.5/0.1 | 60 | 150 | 0 | 20.16 | 49.76 | 18.98 | 87.2 | 88.9 |
|   | pTsOH | 0.1 | 60 | 150 | 13 | 7.13 | 59.24 | 12.31 |  | 91.7 |
|   | H$_3$PO$_3$ | 2.5 | 60 | 150 | 39.6 | 2.51 | 41.68 | 11.62 |  | 95.4 |
| 11 | H$_3$PO$_3$/Ga(OTf)$_3$ | 5/0.005 | 60 | 150 | 12.7 | 13.32 | 55.75 | 14.03 |  | 95.8 |
|   | Ga(OTf)$_3$ | 0.005 | 60 | 150 | 82.18 | 0 | 14.69 | 3.17 |  | 100.0 |
|   | H$_3$PO$_3$ | 5 | 60 | 150 | 24.47 | 5.18 | 49.00 | 15.40 |  | 94.1 |
| 12 | H$_3$PO$_3$/Ga(OTf)$_3$ | 5/0.005 | 120 | 140 | 12.46 | 11.62 | 55.92 | 14.04 |  | 94.0 |
|   | Ga(OTf)$_3$ | 0.005 | 120 | 140 | 78.5 | 0 | 25.16 | 3.77 |  | 99.9 |
|   | H$_3$PO$_3$ | 5 | 120 | 140 | 20.8 | 9.76 | 52.10 | 7.05 |  | 89.7 |
| 13 | H$_3$PO$_3$/Ga(OTf)$_3$ | 5/0.005 | 180 | 130 | 21.1 | 7.22 | 52.88 | 13.90 |  | 95.1 |
|   | Ga(OTf)$_3$ | 0.005 | 180 | 130 | 89.2 | 0 | 10.62 | 1.92 |  | 100.0 |
|   | H$_3$PO$_3$ | 5 | 180 | 130 | 33.2 | 2.91 | 42.61 | 12.81 |  | 91.5 |
| 14 | H$_3$PO$_3$/Ga(OTf)$_3$ | 5/0.01 | 60 | 150 | 4.2 | 15.09 | 58.44 | 14.49 | 89.8 | 92.2 |
|   | Ga(OTf)$_3$ | 0.01 | 60 | 150 | 67.0 | 0.63 | 24.79 | 5.99 |  | 98.4 |
|   | H$_3$PO$_3$ | 5 | 60 | 150 | 24.5 | 5.18 | 49.00 | 15.40 |  | 94.1 |
| 15 | H$_3$PO$_3$/Ga(OTf)$_3$ | 5/0.01 | 120 | 140 | 6.9 | 12.49 | 57.04 | 16.37 | 90.0 | 92.8 |
|   | Ga(OTf)$_3$ | 0.01 | 120 | 140 | 73.7 | 0.31 | 26.01 | 2.97 |  | 99.2 |
|   | H$_3$PO$_3$ | 5 | 120 | 140 | 20.8 | 9.76 | 52.10 | 7.05 |  | 89.7 |
| 16 | H$_3$PO$_3$/Ga(OTf)$_3$ | 5/0.01 | 180 | 130 | 14.2 | 8.76 | 54.24 | 16.60 | 91.0 | 93.8 |
|   | Ga(OTf)$_3$ | 0.01 | 180 | 130 | 81.8 | 0.00 | 14.72 | 2.90 |  | 99.8 |
|   | H$_3$PO$_3$ | 5 | 180 | 130 | 33.2 | 2.91 | 42.61 | 12.81 |  | 91.5 |
| 17 | H$_3$PO$_3$/Ga(OTf)$_3$ | 5/0.05 | 120 | 140 | 0.0 | 24.13 | 47.04 | 18.38 | 86.8 | 89.6 |
|   | Ga(OTf)$_3$ | 0.05 | 120 | 140 | 32.9 | 4.47 | 47.02 | 8.08 |  | 92.5 |
|   | H$_3$PO$_3$ | 5 | 120 | 140 | 20.8 | 9.76 | 52.10 | 7.06 |  | 89.7 |
| 18 | H$_3$PO$_3$/Ga(OTf)$_3$ | 5/0.05 | 60 | 150 | 0.0 | 33.1 | 33.66 | 17.14 |  | 83.9 |
|   | Ga(OTf)$_3$ | 0.05 | 60 | 150 | 28.9 | 6.01 | 44.13 | 8.53 |  | 87.6 |
|   | H$_3$PO$_3$ | 5 | 60 | 150 | 24.5 | 5.18 | 49.00 | 15.37 |  | 94.1 |
| 19 | H$_3$PO$_3$/Al(OTf)$_3$ | 5/0.1 | 60 | 150 | 0.0 | 40.07 | 27.76 | 17.98 |  | 85.8 |
|   | Al(OTf)$_3$ | 0.1 | 60 | 150 | 9.8 | 13.39 | 50.02 | 15.77 |  | 89.0 |
|   | H$_3$PO$_3$ | 5 | 60 | 150 | 24.5 | 5.18 | 49.00 | 15.40 |  | 94.1 |
| 20 | H$_3$PO$_3$/Bi(OTf)$_3$/pTsOH | 5/0.01/0.05 | 60 | 150 | 0.0 | 19.63 | 48.96 | 18.52 |  | 87.1 |
|   | Bi(OTf)$_3$ | 0.01 | 60 | 150 | 74.6 | 0.00 | 19.42 | 4.38 |  | 98.4 |
|   | p-TsOH | 0.05 | 60 | 150 | 37.8 | 2.36 | 43.66 | 9.82 |  | 93.7 |
|   | H$_3$PO$_3$ | 5 | 60 | 150 | 24.47 | 5.18 | 49.00 | 15.40 |  | 94.1 |

TABLE 1-continued

Summary of Co-catalysis Results

| Ex. | Catalysts | Catalyst Load (mol %) | Time (min) | Temp (° C.) | Sorbitol (wt. %) | Isosorbide (wt. %) | 1,4-sorbitan (wt. %) | 2,5-sorbitan(s) (wt. %) | Accountability (%) w/o Catalyst | Accountability (%) + Catalysts |
|---|---|---|---|---|---|---|---|---|---|---|
| 21 | $H_3PO_4/Bi(OTf)_3/$ p-TsOH | 2.5/0.01/0.1 | 60 | 150 | 0.0 | 39.07 | 29.01 | 20.45 | | 88.5 |
| | $Bi(OTf)_3$ | 0.01 | 60 | 150 | 74.6 | 0.00 | 19.42 | 4.38 | | 98.4 |
| | p-TsOH | 0.1 | 60 | 150 | 13 | 7.13 | 59.24 | 12.31 | | 91.7 |
| | $H_3PO_3$ | 2.5 | 60 | 150 | 39.6 | 2.51 | 41.68 | 11.62 | | 95.4 |
| 22 | $H_3PO_3/Hf(OTf)_4/$ pTsOH | 5/0.01/0.05 | 60 | 150 | 0.0 | 29.18 | 43.83 | 13.29 | | 86.3 |
| | $Hf(OTf)_4$ | 0.01 | 60 | 150 | 47.4 | 6.62 | 42.03 | 0.50 | | 96.6 |
| | p-TsOH | 0.05 | 60 | 150 | 37.8 | 2.36 | 43.66 | 9.82 | | 93.7 |
| | $H_3PO_3$ | 5 | 60 | 150 | 24.47 | 5.18 | 49.00 | 15.40 | | 94.1 |

Figure 22:
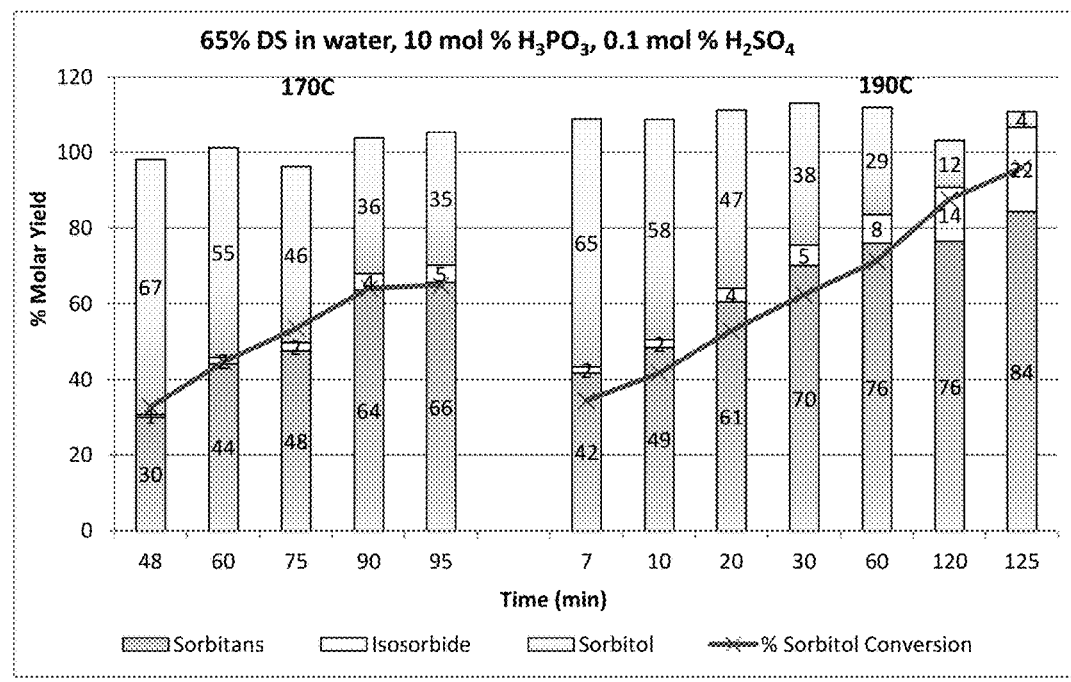
FIG. 22 is a bar graph showing the relative composition and percent accountability of product mixtures for dehydrative cyclization of sorbitol using a combination of 10 mol. % $H_3PO_3$, and 0.1 mol. % $H_2SO_4$ co-catalysis, at different temperatures (170° C. & 190° C.) and for various time periods.
Figure 23:
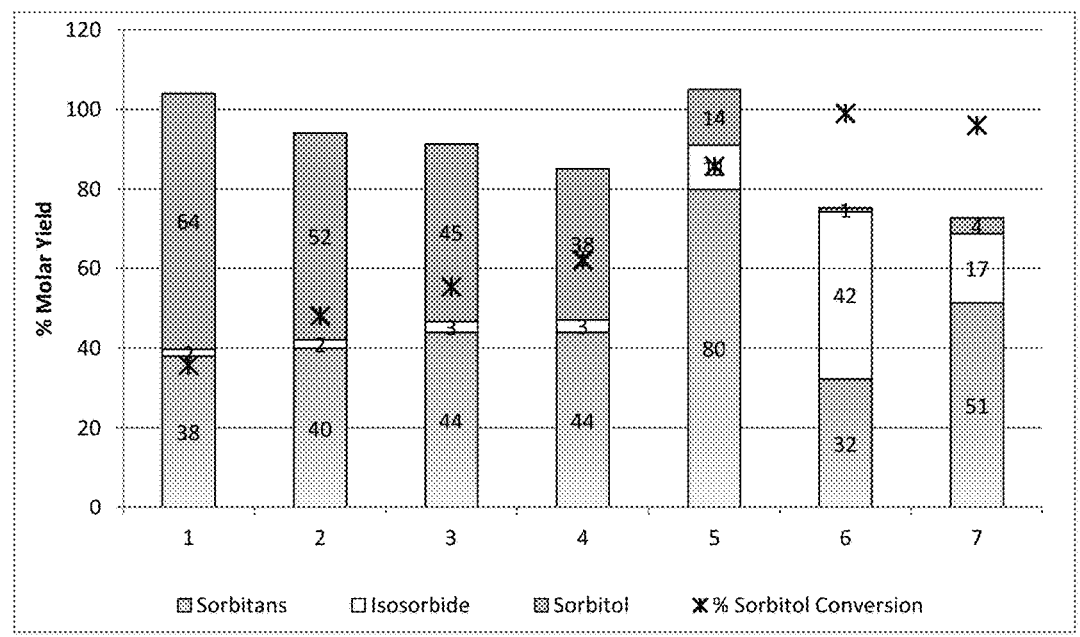
FIG. 23 is a bar graph showing for purposes of comparison the relative composition and percent accountability of product mixtures for dehydrative cyclization of sorbitol using only sulfuric acid catalyst at different catalyst load, temperature, and reaction times.

Two sets of dehydrative cyclization reactions of sorbitol using a mixed acid catalyst of 10 mol. % $H_3PO_3$, and 0.1 mol. % $H_2SO_4$, at 170° C. and 190° C., for various time periods were conducted. The relative composition and percent accountability of product mixtures for the reactions are summarized in Table 2, and presented graphically in FIG. 22.

TABLE 2

| Sample # | Reaction time (min) | Temp. (° C.) | % molar yield | | | | % Sorbitol Conversion | mol % $H_3PO_3$ | mol % $H_2SO_4$ | Color |
|---|---|---|---|---|---|---|---|---|---|---|
| | | | Sorbitans | Isosorbide | Sorbitol | total*** | | | | |
| 1 | 48 | 170 | 30 | 1 | 67 | 98 | 33 | 10.0 | 0.1 | pale yellow |
| 2 | 60 | 169 | 44 | 2 | 55 | 101 | 45 | 10.0 | 0.1 | more gold |
| 3 | 75 | 170 | 48 | 2 | 46 | 96 | 54 | 10.0 | 0.1 | more gold |
| 4 | 90 | 170 | 64 | 4 | 36 | 104 | 64 | 10.0 | 0.1 | more gold |
| 5 final | 95 | 170 | 66 | 5 | 35 | 105 | 65 | 10.0 | 0.1 | more gold |
| 6 | 30 | 190 | 70 | 5 | 38 | 113 | 62 | 10.0 | 0.1 | golden from |
| 7 | 60 | 190 | 76 | 8 | 29 | 112 | 71 | 10.0 | 0.1 | start (5 min) |
| 8 | 120 | 190 | 76 | 14 | 12 | 103 | 88 | 10.0 | 0.1 | and not much |
| 9 final | 125 | 190 | 84 | 22 | 4 | 111 | 96 | 10.0 | 0.1 | color change |

Product accountability was consistently high (>96%) even at the higher temperature. Color did not change dramatically in products obtained at 190° C. from those when the reaction was performed at 170° C. In the present cases, the samples were gold color with no solid formation. Previously, the products of reactions catalyzed without the mixed acid catalysts were generally dark in color and tar-like with high sorbitol conversion. (See for example, International Application No. PCT/US2014/66298, the contents of which are incorporated herein by reference.)

For purposed of comparison, Table 3 shows similar conversions can be obtained using sulfuric acid alone without $H_3PO_3$, in a concentrated solution of sorbitol (~65% DS). The ratio of sorbitans is higher in the presence of $H_3PO_3$ at 170° C. and higher overall accountability at both 170° C. and 190° C. The product mixture at 190° C. with sulfuric acid is darker than that observed at 170° C. The process showed the process works well with sulfuric acid at reasonable reaction times.

| Example | Reaction time (min) | Temp. (° C.) | % molar yield | | | % conversion | mol % $H_3PO_3$ | mol % $H_2SO_4$ | COLOR |
|---|---|---|---|---|---|---|---|---|---|
| | | | Sorbitans | Isosorbide | Sorbitol | | | | |
| 1 | 10 | 170 | 38 | 2 | 64 | 36 | 0 | 2 | bright yellow |
| 2 | 15 | 170 | 40 | 2 | 52 | 48 | 0 | 2 | bright yellow |
| 3 | 20 | 170 | 44 | 3 | 45 | 55 | 0 | 2 | bright yellow |
| 4 | 25 | 170 | 44 | 3 | 38 | 62 | 0 | 2 | bright yellow |
| 5 | 10 | 185 | 80 | 11 | 14 | 86 | 0 | 2 | amber |
| 6 | 30 | 190 | 32 | 42 | 1 | 99 | 0.0 | 2.7 | brown |
| 7 | 10 | 190 | 51 | 17 | 4 | 96 | 0.0 | 1.0 | brown |

2. Conversion Yield and Compositional Accountability

FIGS. 1-20, show in graphical form the data summarized in Table 1. The figures show the percentage of sorbitol converted to isosorbide and percentage of product compositional accountability under various reaction conditions (i.e., temperatures and times) using phosphonic acid ($H_3PO_3$) catalyst, at various catalyst loading levels, and a strong Brønsted acid and/or Lewis acid catalysts, at various catalyst loading levels, alone and in combination with the strong Brønsted acid and/or Lewis acid catalysts.

In aggregate, the data suggests that one can control or modulate time, temperature, and catalyst load to balance and optimize desired target yields and product accountability. The combined catalysts and higher catalyst loadings facilitate quick conversion of the sugar alcohol to its corresponding dehydration product at relatively low temperatures, with minimal reduction in product accountability.

Figure 2:
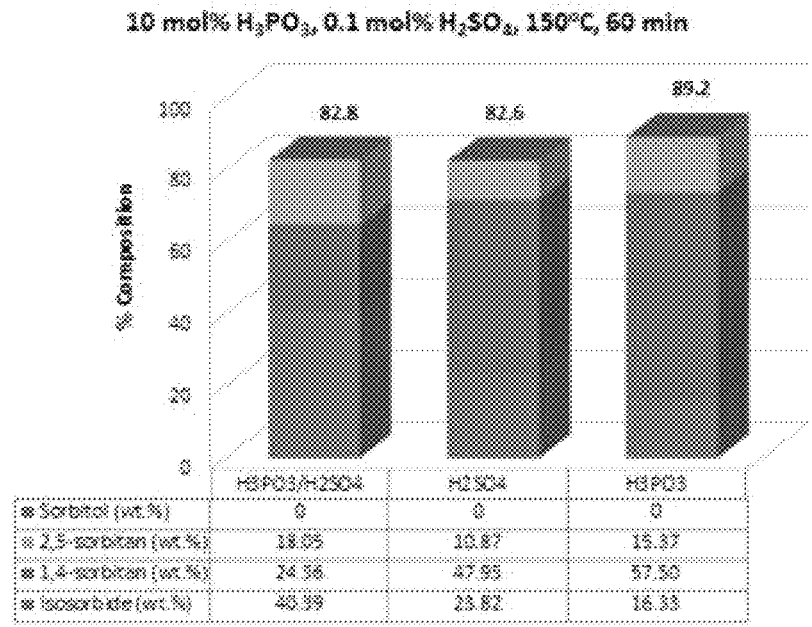
FIG. 2 is a bar graph showing the compositional accountability of the product mixture from three dehydration cyclization reactions of sorbitol catalyzed with 1) 10 mol. % $H_3PO_3$, alone; 2) 0.1 mol. % $H_2SO_4$, alone; and 3) combining the two in a mixed acid catalyst, at 150° C. for 1 h. (60 min.).

In FIG. 1, sorbitol is converted to isosorbide using 10 mol. % $H_3PO_3$, 0.1 mol. % $H_2SO_4$, 140° C., 2 h., in three reactions with each individual acid catalyst separately, and in combination. All of the sorbitol is converted in all three reactions. The amount of isosorbide generated in the phosphonic acid catalysis is about 12.30 wt. % of the reaction product mixture, the sulfuric acid catalysis is about 21.74 wt. % of the reaction product mixture, and in the combined phosphonic and sulfuric acid catalysis is about 35.88 wt. %. The combined acid catalysis generated more of isosorbide when compared to each of the single acid catalysis, while also maintaining a comparable level of compositional accountability for the respective reaction product mixtures of the three acid reactions. The product accountability of each of the reactions does not differ significantly from each other (i.e., 83.6% with $H_3PO_3/H_2SO_4$; 83.3% with $H_2SO_4$; 88.5% with $H_3PO_3$).

In FIG. 2, again, sorbitol is converted to isosorbide using 10 mol. % $H_3PO_3$, 0.1 mol. % $H_2SO_4$, 150° C., 1 h., in three reactions with each individual acid catalyst separately, and in combination. Again, all of the sorbitol is converted in all three reactions. The amount of isosorbide generated in the phosphonic acid catalysis is about 16.33 wt. % of the reaction product mixture, the sulfuric acid catalysis is about 23.82 wt. % of the reaction product mixture, and in the combined phosphonic and sulfuric acid catalysis is about 40.39 wt. %. The combined acid catalysis generated more of isosorbide when compared to each of the single acid catalysis, while maintaining concomitantly a comparable level of compositional accountability for the respective reaction product mixtures of the three acid reactions. The product accountability of each of the reactions ranged from 82.8% with $H_3PO_3/H_2SO_4$; 82.6% with $H_2SO_4$; 89.2% with $H_3PO_3$.

Figure 3:
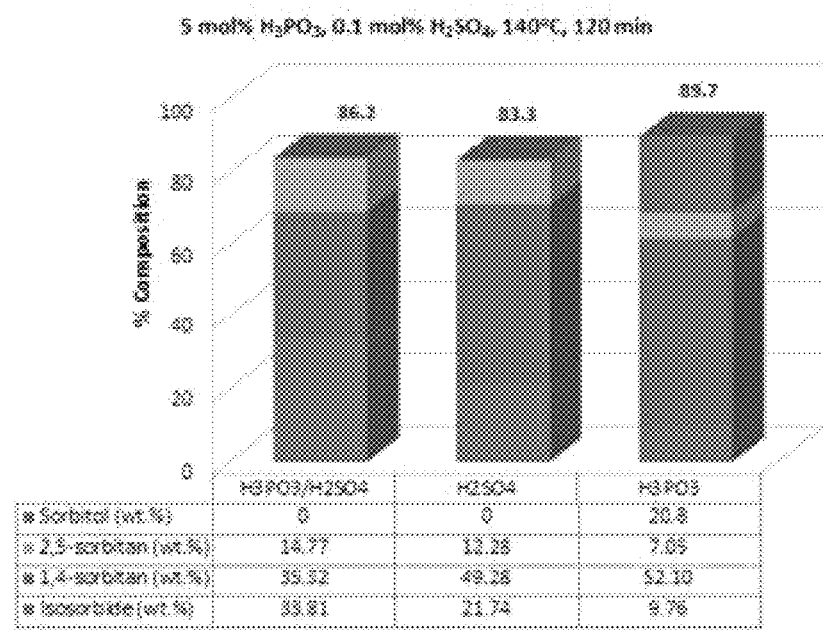
FIG. 3 is a bar graph showing the compositional accountability of the product mixture from three dehydration cyclization reactions of sorbitol catalyzed with 1) 5 mol. % $H_3PO_3$, alone, 2) 0.1 mol. % $H_2SO_4$, alone, and 3) combining the two in a mixed acid catalyst, at 140° C. for 2 h. (120 min.).

In FIG. 3, sorbitol is converted to isosorbide using 5 mol. % $H_3PO_3$, 0.1 mol. % $H_2SO_4$, 140° C., 2 h., in three reactions with each individual acid catalyst separately, and in combination. The amount of isosorbide generated in the phosphonic acid catalysis is about 9.76 wt. % of the reaction product mixture, the sulfuric acid catalysis is about 21.74 wt. % of the reaction product mixture, and in the combined phosphonic and sulfuric acid catalysis is about 33.81 wt. %. The combined acid catalysis generated more of isosorbide when compared to each of the single acid catalysis, while maintaining concomitantly a comparable level of compositional accountability for the respective reaction product mixtures of the three acid reactions. The product accountability of each of the reactions ranged from 86.2% with $H_3PO_3/H_2SO_4$; 83.3% with $H_2SO_4$; 89.7% with $H_3PO_3$. All of the sorbitol is consumed in the combined acid and $H_2SO_4$ catalysis, while a significant percent remains unreacted for the $H_3PO_3$ (20.8%) single acid catalysis.

Figure 4:
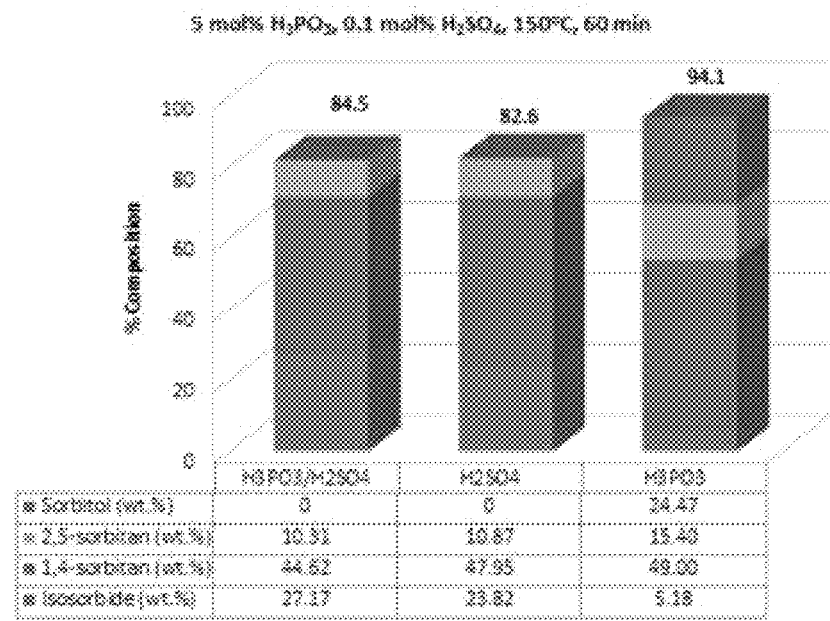
FIG. 4 is a bar graph showing the compositional accountability of the product mixture from three dehydration cyclization reactions of sorbitol catalyzed with 1) 5 mol. % $H_3PO_3$, alone, 2) 0.1 mol. % $H_2SO_4$, alone, and 3) combining the two in a mixed acid catalyst, at 150° C. for 1 h. (60 min.).

In FIG. 4, sorbitol is converted to isosorbide using 5 mol. % $H_3PO_3$, 0.1 mol. % $H_2SO_4$, 150° C., 1 h., in three reactions with each individual acid catalyst separately, and in combination. The amount of isosorbide generated in the phosphonic acid catalysis is about 5.18 wt. % of the reaction product mixture, the sulfuric acid catalysis is about 23.82 wt. % of the reaction product mixture, and in the combined phosphonic and sulfuric acid catalysis is about 27.17 wt. %. The combined acid catalysis generated more of isosorbide when compared to each of the single acid catalysis, while maintaining concomitantly a comparable level of compositional accountability for the respective reaction product mixtures of the three acid reactions. The product accountability of each of the reactions ranged from 84.5% with $H_3PO_3/H_2SO_4$; 82.6% with $H_2SO_4$; 94.1% with $H_3PO_3$. All of the sorbitol is consumed in the combined acid and $H_2SO_4$ catalysis, while a significant percent remains unreacted for the $H_3PO_3$ (24.47%) single acid catalysis.

Figure 5:
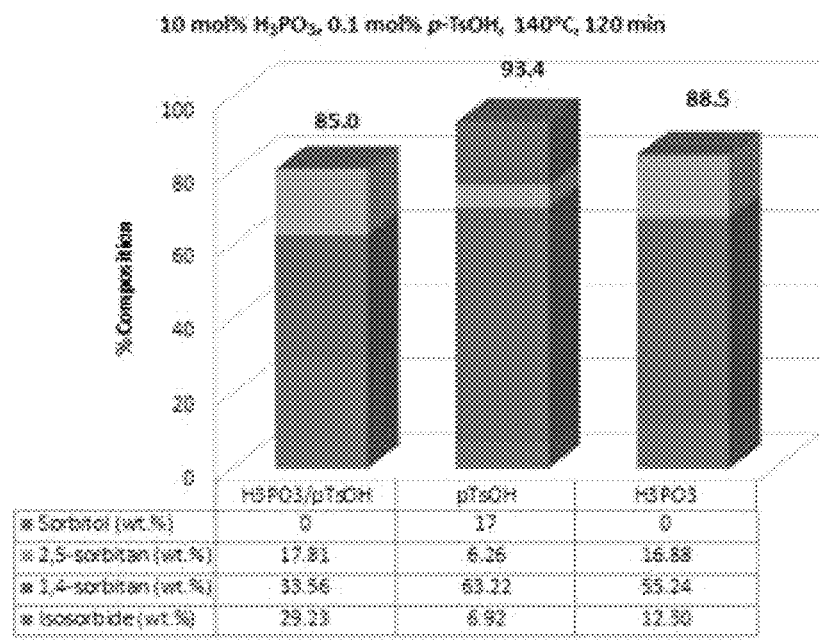
FIG. 5 is a bar graph showing the compositional accountability of the product mixture from three dehydration cyclization reactions of sorbitol catalyzed with 1) 10 mol. % $H_3PO_3$, alone, 2) 0.1 mol. % p-TsOH, alone, and 3) combining the two in a mixed acid catalyst, at 140° C. for 2 h. (120 min.).

In FIG. 5, sorbitol is converted to isosorbide using 10 mol. % $H_3PO_3$, 0.1 mol. % p-TsOH, 140° C., 2 h., in three reactions with each individual acid catalyst separately, and in combination. The amount of isosorbide generated in the phosphonic acid catalysis is about 12.30 wt. % of the reaction product mixture, the p-TsOH catalysis is about 6.92 wt. % of the reaction product mixture, and in the combined p-TsOH and phosphonic acid catalysis is about 29.23 wt. %. The combined acid catalysis generated about 2-3 times more isosorbide when compared to the single acid catalysis, while maintaining concomitantly a comparable level of compositional accountability for the respective reaction product mixtures of the three acid reactions. The product accountability of each of the reactions ranged from 85.0% with $H_3PO_3$/p-TsOH; 93.4% with p-TsOH; 88.5% with $H_3PO_3$. All of the sorbitol is consumed in the combined acid and $H_3PO_3$ catalysis, while a significant percent remains unreacted for the p-TsOH (17%) single acid catalysis.

Figure 6:
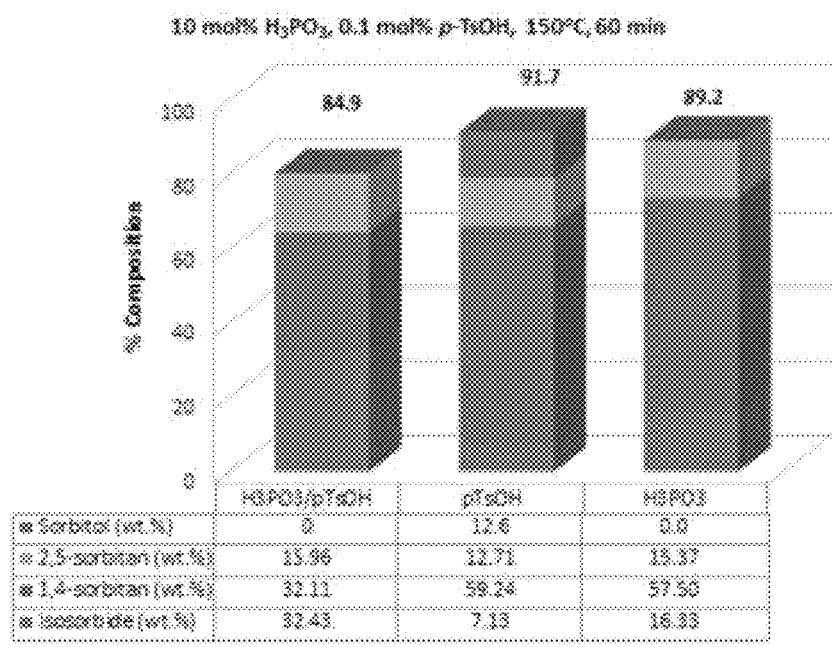
FIG. 6 is a bar graph showing the compositional accountability of the product mixture from three dehydration cyclization reactions of sorbitol catalyzed with 1) 10 mol. % $H_3PO_3$, alone, 2) 0.1 mol. % p-TsOH, alone, and 3) combining the two in a mixed acid catalyst, at 150° C. for 1 h. (60 min.).

In FIG. 6, sorbitol is converted to isosorbide using 10 mol. % $H_3PO_3$, 0.1 mol. % p-TsOH, 150° C., 1 h., in three reactions with each individual acid catalyst separately and in combination. The amount of isosorbide generated in the phosphonic acid catalysis is about 16.33 wt. % of the reaction product mixture, the p-TsOH catalysis is about 7.13 wt. % of the reaction product mixture, and in the combined p-TsOH and phosphonic acid catalysis is about 32.43 wt. %. The combined acid catalysis generated about 2-3 times more of isosorbide when compared to the single acid catalysis, while maintaining concomitantly a comparable level of compositional accountability for the respective reaction product mixtures of the three acid reactions. The product accountability of each of the reactions ranged from 84.9% with $H_3PO_3$/p-TsOH; 91.7% with p-TsOH; 89.2% with $H_3PO_3$. All of the sorbitol is consumed in the combined acid and $H_3PO_3$ catalysis, while a significant percent remains unreacted for the p-TsOH (12.6%) single acid catalysis.

Figure 7:
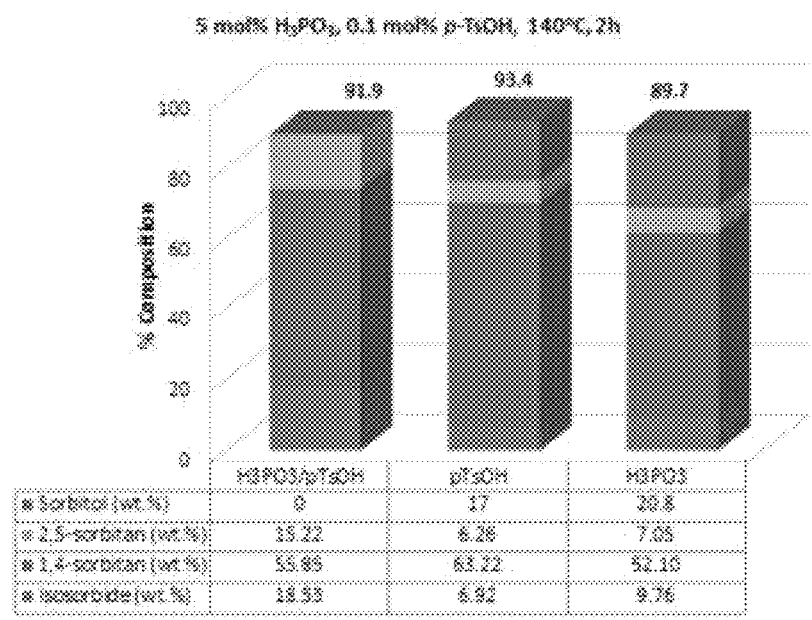
FIG. 7 is a bar graph showing the compositional accountability of the product mixture from three dehydration cyclization reactions of sorbitol catalyzed with 1) 5 mol. % $H_3PO_3$, alone, 2) 0.1 mol. % p-TsOH, alone, and 3) combining the two in a mixed acid catalyst, at 140° C. for 2 h. (120 min.).

In FIG. 7, sorbitol is converted to isosorbide using 5 mol. % $H_3PO_3$, 0.1 mol. % p-TsOH, 140° C., 2 h., in three reactions with each individual acid catalyst separately, and in combination. The amount of isosorbide generated in the phosphonic acid catalysis is about 9.76 wt. % of the reaction product mixture, the p-TsOH catalysis is about 6.92 wt. % of the reaction product mixture, and in the combined p-TsOH and phosphonic acid catalysis is about 18.53 wt. %. The combined acid catalysis generated about 2-3 times more of isosorbide when compared to the single acid catalysis, while maintaining concomitantly a comparable level of compositional accountability for the respective reaction product mixtures of the three acid reactions. The product accountability of each of the reactions ranged from 18.53% with $H_3PO_3$/p-TsOH; 6.92% with p-TsOH; 9.76% with $H_3PO_3$. All of the sorbitol is consumed in the combined acid catalysis, while a significant percent remains unreacted for both the $H_3PO_3$ (20.8%) and p-TsOH (17%) single acid catalysis. All of the sorbitol is consumed in the combined acid catalysis, while a significant percent remains unreacted for both the $H_3PO_3$ (20.8%) and p-TsOH (17%) single acid catalysis.

Figure 8:
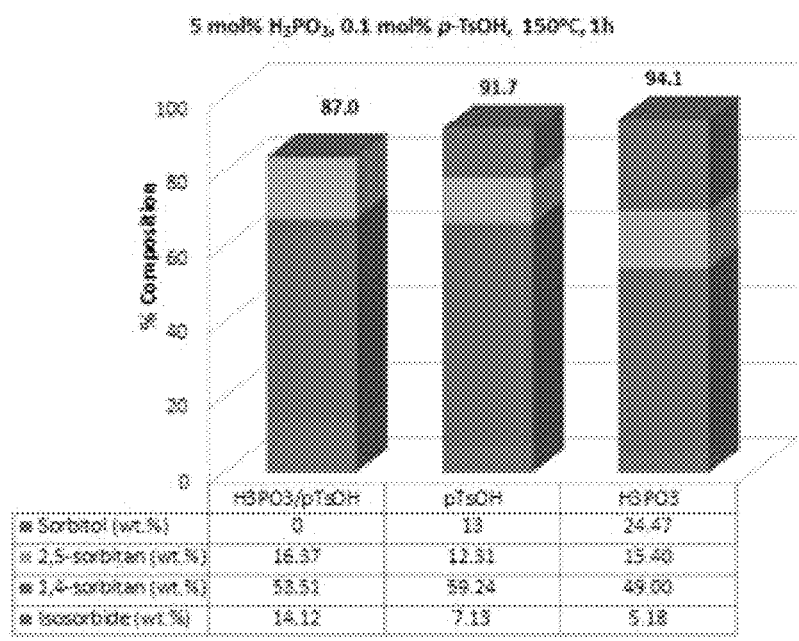
FIG. 8 is a bar graph showing the compositional accountability of the product mixture from three dehydration cyclization reactions of sorbitol catalyzed with 1) 5 mol. % $H_3PO_3$, alone, 2) 0.1 mol. % p-TsOH, alone, and 3) combining the two in a mixed acid catalyst, at 150° C. for 1 h. (60 min.).

In FIG. 8, sorbitol is converted to isosorbide using 5 mol. % $H_3PO_3$, 0.1 mol. % p-TsOH, 150° C., 1 h., in three reactions with each individual acid catalyst separately, and in combination. The amount of isosorbide generated in the phosphonic acid catalysis is about 5.18 wt. % of the reaction product mixture, the p-TsOH catalysis is about 7.13 wt. % of the reaction product mixture, and in the combined p-TsOH and phosphonic acid catalysis is about 14.12 wt. %. The combined acid catalysis generated about 2-3 times more of isosorbide when compared to the single acid catalysis, while maintaining concomitantly a comparable level of compositional accountability for the respective reaction product mixtures of the three acid reactions. The product accountability of each of the reactions ranged from 87.0% with $H_3PO_3$/p-TsOH; 91.7% with p-TsOH; 94.1% with $H_3PO_3$. All of the sorbitol is consumed in the combined acid catalysis, while a significant percent remains unreacted for both the $H_3PO_3$ (24.47 wt. %) and p-TsOH (13 wt. %) single acid catalysis. All of the sorbitol is consumed in the combined acid catalysis, while a significant percent remains unreacted for both the $H_3PO_3$ (24.47%) and p-TsOH (13%) single acid catalysis.

Figure 9:
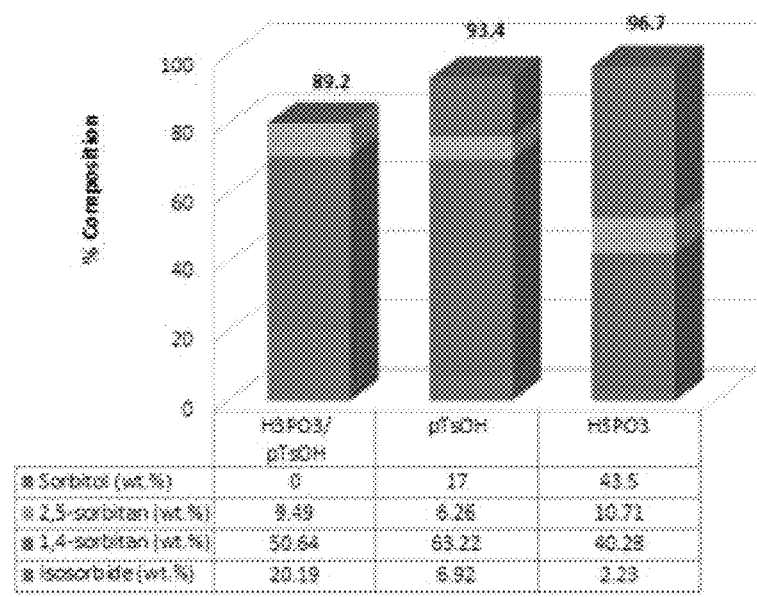
FIG. 9 is a bar graph showing the compositional accountability of the product mixture from three dehydration cyclization reactions of sorbitol catalyzed with 1) 2.5 mol. % $H_3PO_3$, alone, 2) 0.1 mol. % p-TsOH, alone, and 3) combining the two in a mixed acid catalyst, at 140° C. for 2 h. (120 min.).

In FIG. 9, sorbitol is converted to isosorbide using 2.5 mol. % $H_3PO_3$, 0.1 mol. % p-TsOH, 140° C., 2 h., in three reactions with each individual acid catalyst separately, and in combination. The amount of isosorbide generated in the phosphonic acid catalysis is about 5.18 wt. % of the reaction product mixture, the p-TsOH catalysis is about 7.13 wt. % of the reaction product mixture, and in the combined p-TsOH and phosphonic acid catalysis is about 14.12 wt. %. The combined acid catalysis generated about 2-3 times more of isosorbide when compared to the single acid catalysis, while maintaining concomitantly a comparable level of compositional accountability for the respective reaction product mixtures of the three acid reactions. The product accountability of each of the reactions ranged from 87.0% with $H_3PO_3$/p-TsOH; 91.7% with p-TsOH; 94.1% with $H_3PO_3$. All of the sorbitol is consumed in the combined acid catalysis, while a significant percent remains unreacted for both the $H_3PO_3$ (43.5 wt. %) and p-TsOH (17 wt. %) single acid catalysis.

Figure 10:
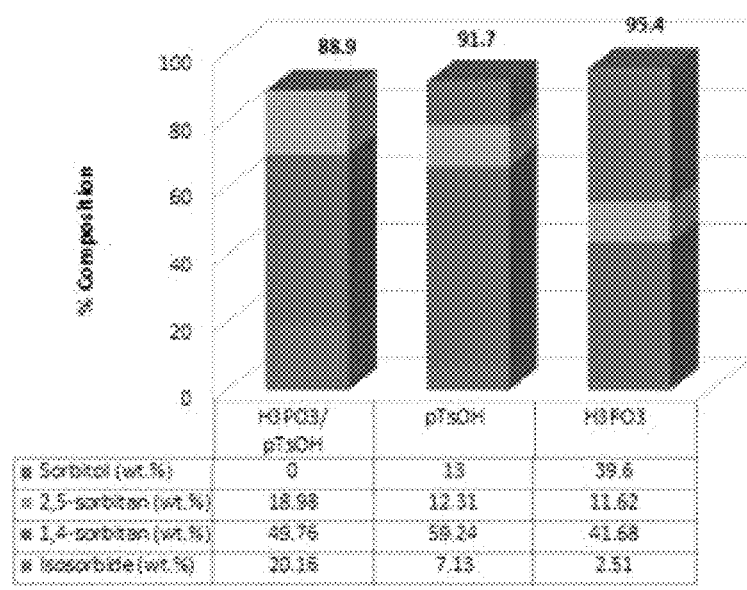
FIG. 10 is a bar graph showing the compositional accountability of the product mixture from three dehydration cyclization reactions of sorbitol catalyzed with 1) 2.5 mol. % $H_3PO_3$, alone, 2) 0.1 mol. % p-TsOH, alone, and 3) combining the two in a mixed acid catalyst, at 150° C. for 1 h. (60 min.).

In FIG. 10, sorbitol is converted to isosorbide using 2.5 mol. % $H_3PO_3$, 0.1 mol. % p-TsOH, 150° C., 1 h., in three reactions with each individual acid catalyst separately, and in combination. The amount of isosorbide generated in the phosphonic acid catalysis is about 2.51 wt. % of the reaction product mixture, the p-TsOH catalysis is about 7.13 wt. % of the reaction product mixture, and in the combined p-TsOH and phosphonic acid catalysis is about 20.16 wt. %. The combined acid catalysis generated about 2-6 times more of isosorbide when compared to the single acid catalysis, while maintaining concomitantly a comparable level of compositional accountability for the respective reaction product mixtures of the three acid reactions. The product accountability of each of the reactions ranged from 87.0% with $H_3PO_3$/p-TsOH; 91.7% with p-TsOH; 94.1% with $H_3PO_3$. All of the sorbitol is consumed in the combined acid catalysis, while a significant percent remains unreacted for both the $H_3PO_3$ (39.6 wt. %) and p-TsOH (13 wt. %) single acid catalysis.

Figure 11:
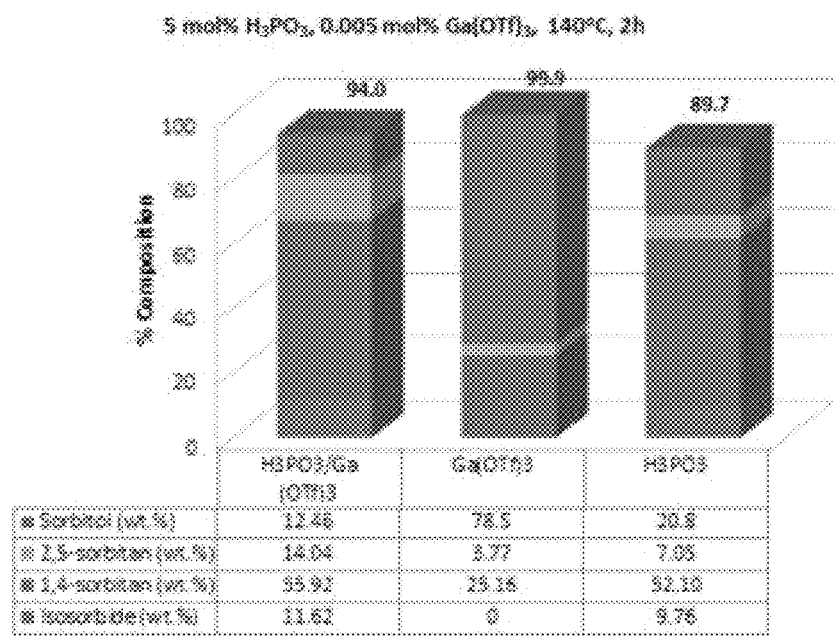
FIG. 11 is a bar graph showing the compositional accountability of the product mixture from three dehydration cyclization reactions of sorbitol catalyzed with 1) 5 mol. % $H_3PO_3$, alone, 2) 0.005 mol. % $Ga(OTf)_3$, alone, and 3) combining the two in a mixed acid catalyst, at 140° C. for 2 h. (120 min.).

In FIG. 11, sorbitol is converted to isosorbide using 5 mol. % $H_3PO_3$, 0.005 mol. % $Ga(OTf)_3$, 140° C., 2 h., in three reactions with each individual acid catalyst separately, and in combination. The amount of isosorbide generated in the phosphonic acid catalysis is about 9.76 wt. % of the reaction product mixture, the $Ga(OTf)_3$ catalysis is 0 wt. % of the reaction product mixture, and in the combined $Ga(OTf)_3$ and phosphonic acid catalysis is about 11.62 wt. %. The combined acid catalysis generated more of isosorbide when compared to the single acid catalysis, while maintaining concomitantly a comparable level of compositional accountability for the respective reaction product mixtures of the three acid reactions. The product accountability of each of the reactions ranged from 94.0% with $H_3PO_3$/$Ga(OTf)_3$; 99.9% with $Ga(OTf)_3$; 89.7% with $H_3PO_3$.

Figure 12:
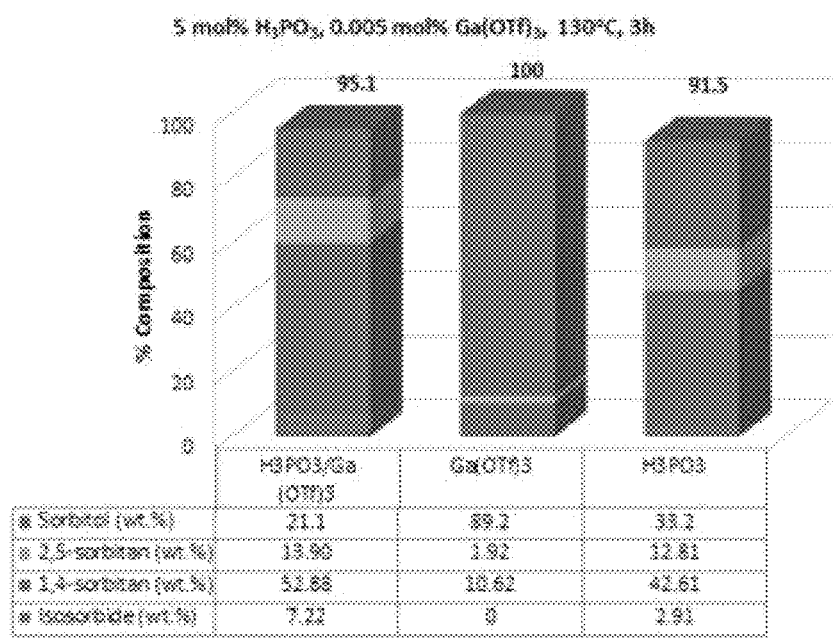
FIG. 12 is a bar graph showing the compositional accountability of the product mixture from three dehydration cyclization reactions of sorbitol catalyzed with 1) 5 mol. % $H_3PO_3$, alone, 2) 0.005 mol. % $Ga(OTf)_3$, alone, and 3) combining the two in a mixed acid catalyst, at 130° C. for 3 h. (180 min.).

In FIG. 12, sorbitol is converted to isosorbide using 5 mol. % $H_3PO_3$, 0.005 mol. % $Ga(OTf)_3$, 130° C., 3 h., in three reactions with each individual acid catalyst separately, and in combination. The amount of isosorbide generated in the phosphonic acid catalysis is about 2.91 wt. % of the reaction product mixture, the $Ga(OTf)_3$ catalysis is 0 wt. % of the reaction product mixture, and in the combined $Ga(OTf)_3$ and phosphonic acid catalysis is about 7.22 wt. %. The combined acid catalysis generated more of isosorbide when compared to the single acid catalysis, while maintaining concomitantly a comparable level of compositional accountability for the respective reaction product mixtures of the three acid reactions. The product accountability of each of the reactions ranged from 95.1% with $H_3PO_3$/$Ga(OTf)_3$; 100% with $Ga(OTf)_3$; 91.5% with $H_3PO_3$.

Figure 13:
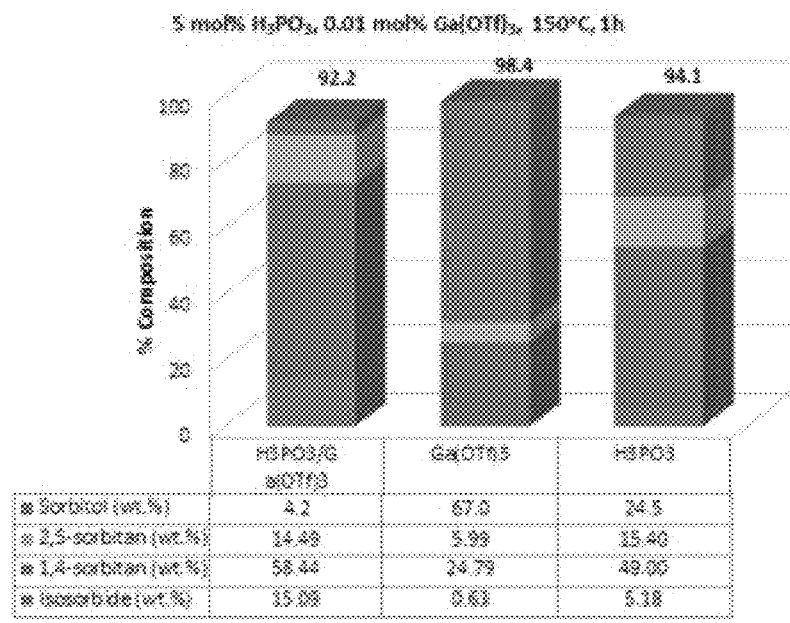
FIG. 13 is a bar graph showing the compositional accountability of the product mixture from three dehydration cyclization reactions of sorbitol catalyzed with 1) 5 mol. % $H_3PO_3$, alone, 2) 0.01 mol. % $Ga(OTf)_3$, alone, and 3) combining the two in a mixed acid catalyst, at 110° C. for 1 h. (60 min.).

In FIG. 13, sorbitol is converted to isosorbide using 5 mol. % $H_3PO_3$, 0.01 mol. % $Ga(OTf)_3$, 150° C., 1 h., in three reactions with each individual acid catalyst separately, and in combination. The amount of isosorbide generated in the phosphonic acid catalysis is about 5.18 wt. % of the reaction product mixture, the $Ga(OTf)_3$ catalysis is about 0.63 wt. % of the reaction product mixture, and in the combined $Ga(OTf)_3$ and phosphonic acid catalysis is about 15.09 wt. %. The combined acid catalysis generated more of isosorbide when compared to the single acid catalysis, while maintaining concomitantly a comparable level of compositional accountability for the respective reaction product mixtures of the three acid reactions. The product accountability of each of the reactions ranged from 92.2% with $H_3PO_3$/$Ga(OTf)_3$; 98.4% with $Ga(OTf)_3$; 94.1% with $H_3PO_3$.

Figure 14:
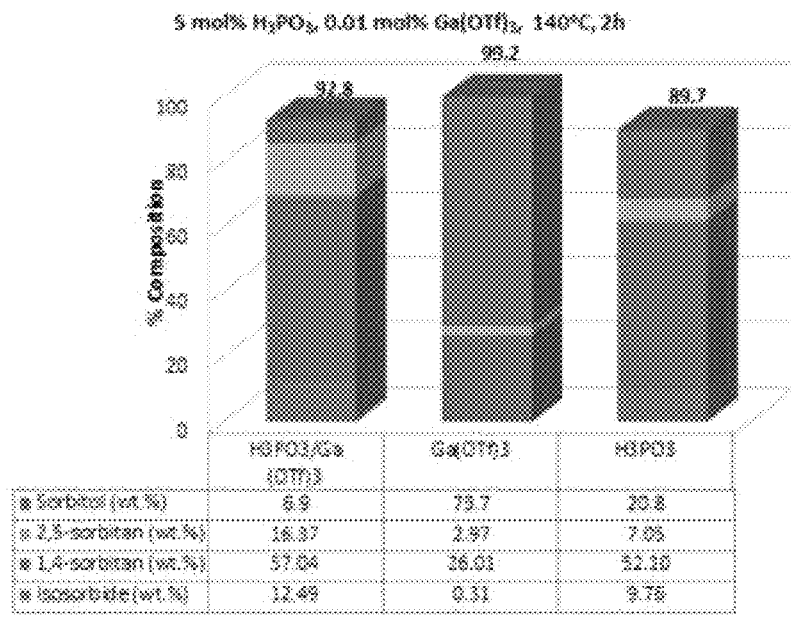
FIG. 14 is a bar graph showing the compositional accountability of the product mixture from three dehydration cyclization reactions of sorbitol catalyzed with 1) 5 mol. % $H_3PO_3$, alone, 2) 0.01 mol. % $Ga(OTf)_3$, alone, and 3) combining the two in a mixed acid catalyst, at 140° C. for 2 h. (120 min.).

In FIG. 14, sorbitol is converted to isosorbide using 5 mol. % $H_3PO_3$, 0.01 mol. % $Ga(OTf)_3$, 140° C., 2 h., in three reactions with each individual acid catalyst separately, and in combination. The amount of isosorbide generated in the phosphonic acid catalysis is about 9.76 wt. % of the reaction product mixture, the $Ga(OTf)_3$ catalysis is about 0.31 wt. % of the reaction product mixture, and in the combined $Ga(OTf)_3$ and phosphonic acid catalysis is about 12.49 wt. %. The combined acid catalysis generated more of isosorbide when compared to the single acid catalysis, while maintaining concomitantly a comparable level of compositional accountability for the respective reaction product mixtures of the three acid reactions. The product accountability of each of the reactions ranged from 92.2% with $H_3PO_3/Ga(OTf)_3$; 98.4% with $Ga(OTf)_3$; 94.1% with $H_3PO_3$.

Figure 15:
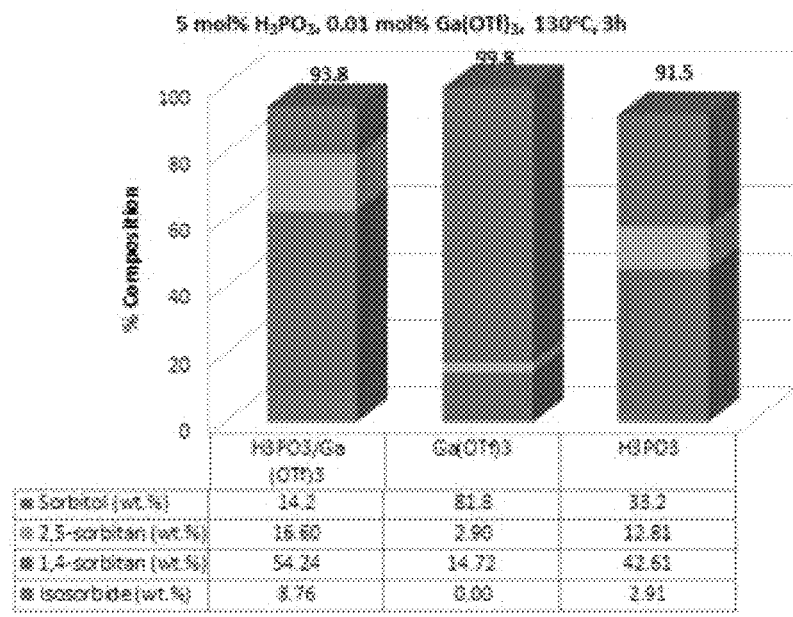
FIG. 15 is a bar graph showing the compositional accountability of the product mixture from three dehydration cyclization reactions of sorbitol catalyzed with 1) 5 mol. % $H_3PO_3$, alone, 2) 0.01 mol. % $Ga(OTf)_3$, alone, and 3) combining the two in a mixed acid catalyst, at 130° C. for 3 h. (180 min.).

In FIG. 15, sorbitol is converted to isosorbide using 5 mol. % $H_3PO_3$, 0.01 mol. % $Ga(OTf)_3$, 130° C., 3 h., in three reactions with each individual acid catalyst separately, and in combination. The amount of isosorbide generated in the phosphonic acid catalysis is about 2.91 wt. % of the reaction product mixture, the $Ga(OTf)_3$ catalysis is 0.1 wt. % of the reaction product mixture, and in the combined $Ga(OTf)_3$ and phosphonic acid catalysis is about 8.76 wt. %. The combined acid catalysis generated more of isosorbide when compared to the single acid catalysis, while maintaining concomitantly a comparable level of compositional accountability for the respective reaction product mixtures of the three acid reactions. The product accountability of each of the reactions ranged from 93.8% with $H_3PO_3/Ga(OTf)_3$; 99.8% with $Ga(OTf)_3$; 91.5% with $H_3PO_3$.

Figure 16:
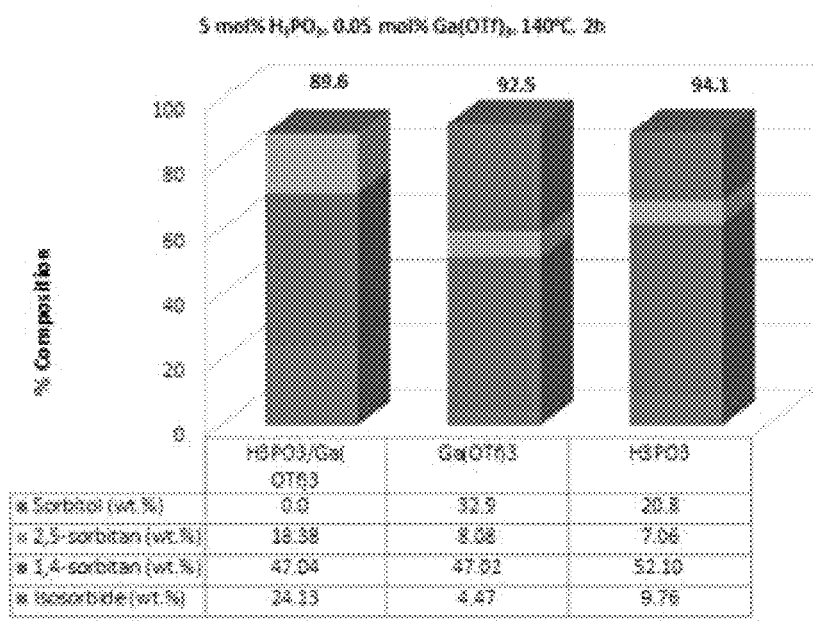
FIG. 16 is a bar graph showing the compositional accountability of the product mixture from three dehydration cyclization reactions of sorbitol catalyzed with 1) 5 mol. % $H_3PO_3$, alone, 2) 0.05 mol. % $Ga(OTf)_3$, alone, and 3) combining the two in a mixed acid catalyst, at 140° C. for 2 h. (120 min.).

In FIG. 16, sorbitol is converted to isosorbide using 5 mol. % $H_3PO_3$, 0.05 mol. % $Ga(OTf)_3$, 140° C., 2 h., in three reactions with each individual acid catalyst separately, and in combination. The amount of isosorbide generated in the phosphonic acid catalysis is about 9.76 wt. % of the reaction product mixture, the $Ga(OTf)_3$ catalysis is about 4.47 wt. % of the reaction product mixture, and in the combined $Ga(OTf)_3$ and phosphonic acid catalysis is about 24.13 wt. %. The combined acid catalysis generated more of isosorbide when compared to the single acid catalysis, while maintaining concomitantly a comparable level of compositional accountability for the respective reaction product mixtures of the three acid reactions. The product accountability of each of the reactions ranged from 89.6% with $H_3PO_3/Ga(OTf)_3$; 92.5% with $Ga(OTf)_3$; 94.1% with $H_3PO_3$. All of the sorbitol is consumed in the combined acid catalysis, while a significant percent remains unreacted for both the $H_3PO_3$ (20.8 wt. %) and $Ga(OTf)_3$ (32.9 wt. %) single acid catalysis.

Figure 17:
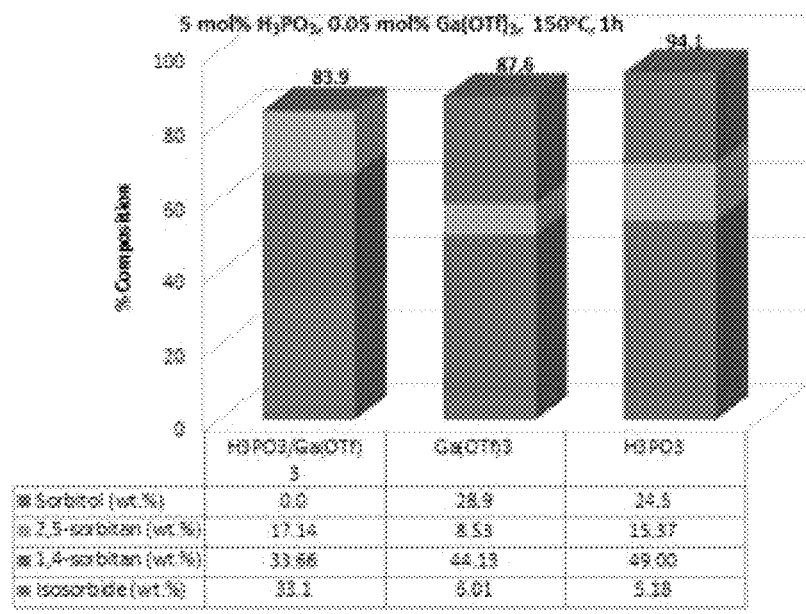
FIG. 17 is a bar graph showing the compositional accountability of the product mixture from three dehydration cyclization reactions of sorbitol catalyzed with 1) 5 mol. % $H_3PO_3$, alone, 2) 0.05 mol. % $Ga(OTf)_3$, alone, and 3) combining the two in a mixed acid catalyst, at 150° C. for 1 h. (60 min.).

In FIG. 17, sorbitol is converted to isosorbide using 5 mol. % $H_3PO_3$, 0.05 mol. % $Ga(OTf)_3$, 150° C., 1 h., in three reactions with each individual acid catalyst separately, and in combination. The amount of isosorbide generated in the phosphonic acid catalysis is about 5.18 wt. % of the reaction product mixture, the $Ga(OTf)_3$ catalysis is about 6.01 wt. % of the reaction product mixture, and in the combined $Ga(OTf)_3$ and phosphonic acid catalysis is about 33.1 wt. %. The combined acid catalysis generated about 5-6 times more of isosorbide when compared to the single acid catalysis, while maintaining concomitantly a comparable level of compositional accountability for the respective reaction product mixtures of the three acid reactions. The product accountability of each of the reactions ranged from 83.9% with $H_3PO_3/GA(OTf)_3$; 87.6% with $Ga(OTf)_3$; 94.1% with $H_3PO_3$. All of the sorbitol is consumed in the combined acid catalysis, while a significant percent remains unreacted for both the $H_3PO_3$ (24.5 wt. %) and $Ga(OTf)_3$ (28.9 wt. %) single acid catalysis.

Figure 18:
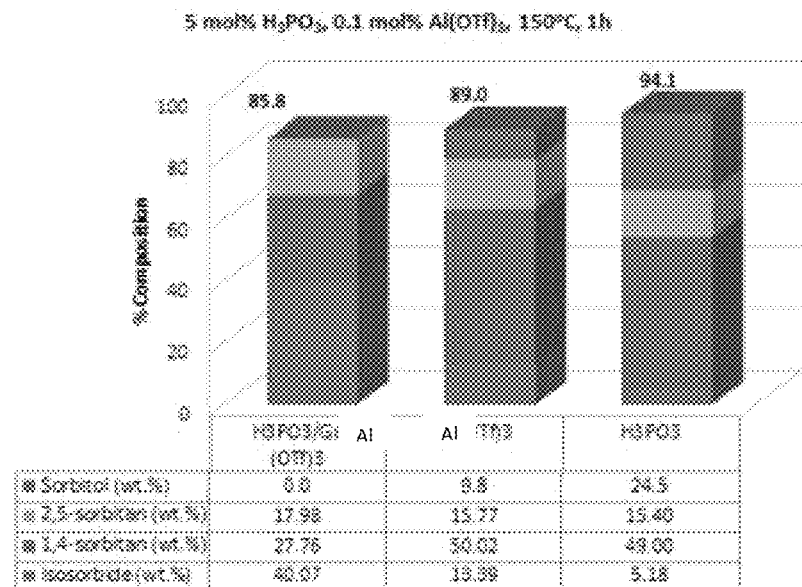
FIG. 18 is a bar graph showing the compositional accountability of the product mixture from three dehydration cyclization reactions of sorbitol catalyzed with 1) 5 mol. % $H_3PO_3$, alone, 2) 0.1 mol. % $Ga(OTf)_3$, alone, and 3) combining the two in a mixed acid catalyst, at 150° C. for 1 h. (60 min.).

In FIG. 18, sorbitol is converted to isosorbide using 5 mol. % $H_3PO_3$, 0.1 mol. % $Al(OTf)_3$, 150° C., 1 h., in three reactions with each individual acid catalyst separately, and in combination. The amount of isosorbide generated in the phosphonic acid catalysis is about 5.18 wt. % of the reaction product mixture, the $Al(OTf)_3$ catalysis is about 13.39 wt. % of the reaction product mixture, and in the combined $Al(OTf)_3$ and phosphonic acid catalysis is about 40.07 wt. %. The combined acid catalysis generated about 5-6 times more of isosorbide when compared to the single acid catalysis, while maintaining concomitantly a comparable level of compositional accountability for the respective reaction product mixtures of the three acid reactions. The product accountability of each of the reactions ranged from 85.8% with $H_3PO_3/Al(OTf)_{03}$; 89.0% with $Al(OTf)_3$; 94.1% with $H_3PO_3$. All of the sorbitol is consumed in the combined acid catalysis, while a significant percent remains unreacted for both the $H_3PO_3$ (24.5 wt. %) and $Al(OTf)_3$ (9.8 wt. %) single acid catalysis.

Figure 19:
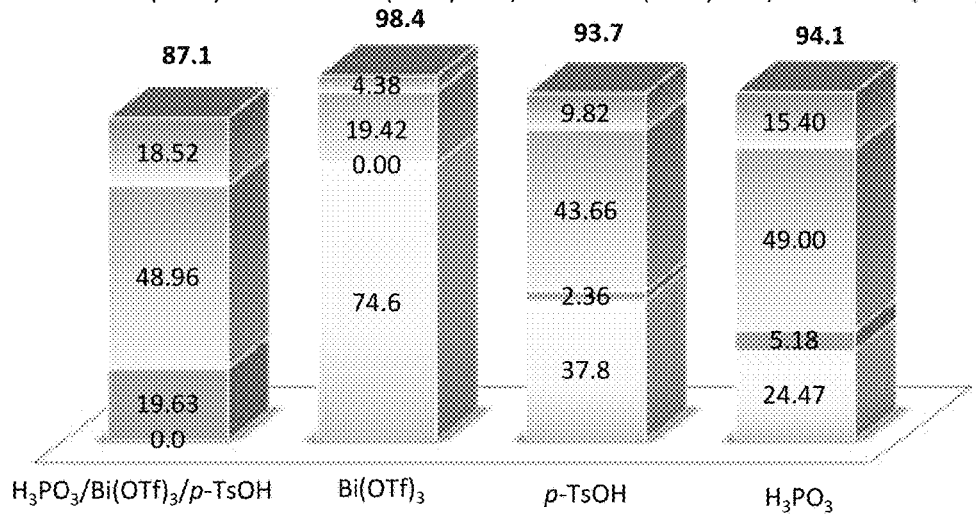
FIG. 19 is a bar graph showing the relative composition and percent accountability of product mixtures for dehydrative cyclization of sorbitol using three different catalysts in combination and each alone: 5 mol. % $H_3PO_3$, 0.01 mol. % $Bi(OTf)_3$, and 0.05 mol. % p-TsOH, 150° C., 1 h. (60 min.).

In FIG. 19, sorbitol is converted to isosorbide using 5 mol. % $H_3PO_3$, 0.01 mol. % $Bi(OTf)_3$, 0.05 mol. % p-TsOH, 150° C., 1 h., in four reactions with each individual acid catalyst separately, and in combination. The amount of isosorbide generated in the phosphonic acid catalysis is about 5.18 wt. % of the reaction product mixture, the $Bi(OTf)_3$ catalysis is 0 wt. % of the reaction product mixture, the p-TsOH catalysis is 2.36 wt. % of the reaction product mixture, and in the combined $Bi(OTf)_3$, p-TsOH and phosphonic acid catalysis is about 19.63 wt. %. The combined acid catalysis generated about 5-6 times more of isosorbide when compared to the single acid catalysis, while maintaining concomitantly a comparable level of compositional accountability for the respective reaction product mixtures of the three acid reactions. The product accountability of each of the reactions ranged from 87.1% with $H_3PO_3/Bi(OTf)_3$/p-TsOH; 98.4% with $Bi(OTf)_3$; 93.7% p-TsOH; 94.1% with $H_3PO_3$. All of the sorbitol is consumed in the combined acid catalysis, while a significant percent remains unreacted for both the $H_3PO_3$ (24.47 wt. %), $Bi(OTf)_3$ (74.6 wt. %), and p-TsOH (37.8 wt. %) single acid catalysis.

Figure 20:
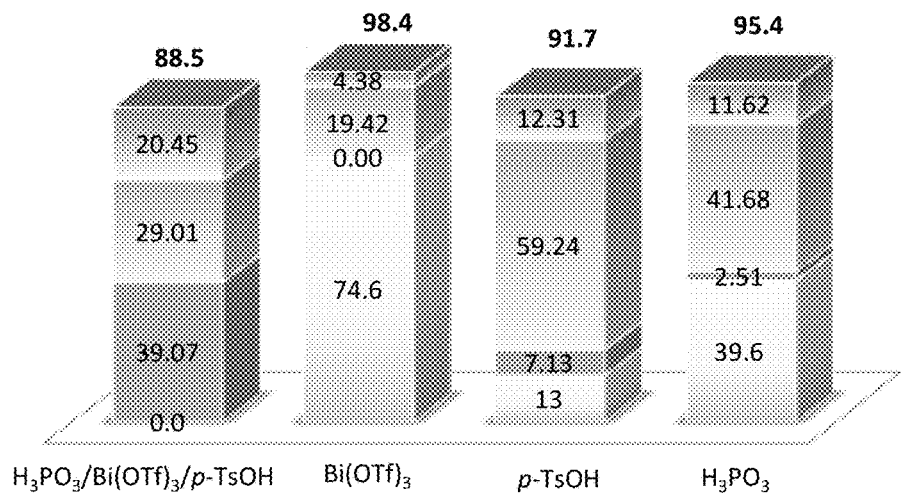
FIG. 20 is a bar graph showing the relative composition and percent accountability of product mixtures for dehydrative cyclization of sorbitol using three different catalysts in combination and each alone: 2.5 mol. % $H_3PO_3$, 0.01 mol. % $Bi(OTf)_3$, and 0.1 mol. % p-TsOH, 150° C., 1 h. (60 min.).

In FIG. 20, sorbitol is converted to isosorbide using 2.5 mol. % $H_3PO_3$, 0.01 mol. % $Bi(OTf)_3$, 0.1 mol. % p-TsOH, 150° C., 1 h., in four reactions with each individual acid catalyst separately, and in combination. The amount of isosorbide generated in the phosphonic acid catalysis is about 2.51 wt. % of the reaction product mixture, the $Bi(OTf)_3$ catalysis is 0 wt. % of the reaction product mixture, the p-TsOH catalysis is 7.13 wt. % of the reaction product mixture, and in the combined $Bi(OTf)_3$, p-TsOH and phosphonic acid catalysis is about 39.07 wt. %. The combined acid catalysis generated about 5-10 times more of isosorbide when compared to the single acid catalysis, while maintaining concomitantly a comparable level of compositional accountability for the respective reaction product mixtures of the three acid reactions. The product accountability of each of the reactions ranged from 88.5% with $H_3PO_3$/Bi $(OTf)_3$/p-TsOH; 98.4% with $Bi(OTf)_3$; 91.7% with p-TsOH; 95.4% with $H_3PO_3$. All of the sorbitol is consumed in the combined multi-acid catalysis, while a significant percent remains unreacted for both the $H_3PO_3$ (39.6 wt. %), $Bi(OTf)_3$ (74.6 wt. %), and p-TsOH (13 wt. %) single acid catalysis.

Figure 21:
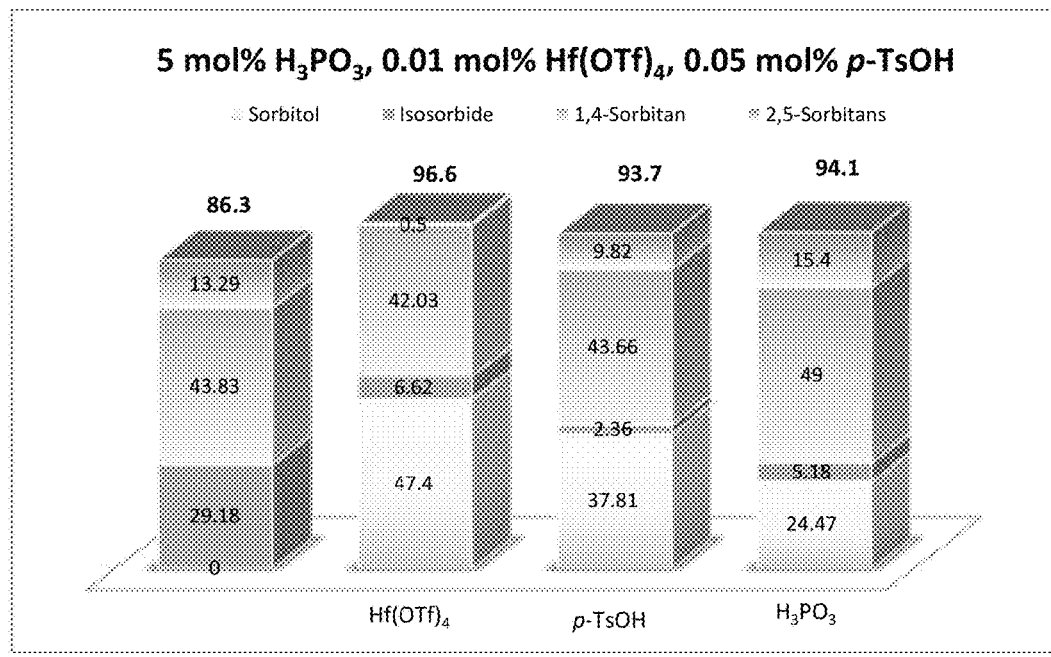
FIG. 21 is a bar graph showing the relative composition and present accountability of product mixtures for dehydrative cyclization of sorbitol using three different catalysts in combination and each alone: 5 mol. % $H_3PO_3$, 0.01 mol. % $Hf(OTf)_4$, and 0.05 mol. % p-TsOH, 150° C., 1 h. (60 min.).

In FIG. 21, sorbitol is converted to isosorbide using 5 mol. % $H_3PO_3$, 0.01 mol. % $Hf(OTf)_4$, 0.05 mol. % p-TsOH, 150° C., 1 h., in four reactions with each individual acid catalyst separately, and in combination. The amount of isosorbide generated in the phosphonic acid catalysis is about 5.18 wt. % of the reaction product mixture, the $Hf(OTf)_4$ catalysis is about 6.62 wt. % of the reaction product mixture, the p-TsOH catalysis is 2.36 wt. % of the reaction product mixture, and in the combined $Hf(OTf)_4$, p-TsOH and phosphonic acid catalysis is about 29.18 wt. %. The combined acid catalysis generated about 5-10 times more of isosorbide when compared to the single acid catalysis, while maintaining concomitantly a comparable level of compositional accountability for the respective reaction product mixtures of the three acid reactions. The product accountability of each of the reactions ranged from 86.3% with $H_3PO_3$/Bi(OTf)$_3$/p-TsOH; 96.6% with Hf(OTf)$_4$, 93.7% with p-TsOH; 94.1% with $H_3PO_3$. All of the sorbitol is consumed in the combined multi-acid catalysis, while a significant percent remains unreacted for both the $H_3PO_3$ (24.47 wt. %), Hf(OTf)$_4$ (47.4 wt. %), and p-TsOH (37.81 wt. %) single acid catalysis.

For comparison, Table 4 summarizes the catalysis results for dehydrative cyclization of sorbitol to isosorbide using sulfuric acid alone.

TABLE 4

$H_2SO_4$

| Load (mol %) | Time (min) | Temp (° C.) | Sorbitol (wt. %) | Iso-sorbide (wt. %) | 1,4-sorbitan (wt. %) | 2,5-sorbitan(s) (wt. %) | Account-ability (%) |
|---|---|---|---|---|---|---|---|
| 0.1 | 180 | 130 | 16 | 5.91 | 63.20 | 6.29 | 91.40 |
| 0.1 | 120 | 140 | 0 | 21.74 | 49.28 | 12.31 | 83.33 |
| 0.1 | 60 | 150 | 0 | 23.82 | 47.95 | 10.87 | 82.64 |
| 0.5 | 180 | 130 | 0 | 34.26 | 37.44 | 9.35 | 81.05 |
| 0.5 | 120 | 140 | 0 | 69.90 | 0.00 | 9.75 | 79.65 |
| 0.5 | 60 | 150 | 0 | 69.58 | 0.00 | 8.26 | 77.84 |
| 1 | 180 | 130 | 0 | 61.23 | 11.23 | 8.04 | 80.50 |
| 1 | 120 | 140 | 0 | 69.67 | 0.00 | 7.77 | 77.44 |
| 1 | 60 | 150 | 0 | 67.82 | 2.21 | 3.59 | 73.62 |

For comparison, Table 5 summarizes the catalysis results for dehydrative cyclization of sorbitol to isosorbide using phosphonic acid alone.

TABLE 5

$H_3PO_3$

| Load (mol %) | Time (min) | Temp (° C.) | Sorbital (wt. %) | Iso-sorbide (wt. %) | 1,4-sorbitan (wt. %) | 2,5-sorbitan(s) (wt. %) | Account-ability (%) |
|---|---|---|---|---|---|---|---|
| 5 | 180 | 130 | 33.16 | 2.91 | 42.61 | 12.81 | 91.49 |
| 5 | 60 | 150 | 24.47 | 5.18 | 49.00 | 15.40 | 94.05 |
| 5 | 120 | 160 | 0 | 35.32 | 35.73 | 17.71 | 88.76 |
| 10 | 120 | 140 | 0 | 12.30 | 58.24 | 17.93 | 88.47 |
| 10 | 60 | 150 | 0 | 16.33 | 57.50 | 15.37 | 89.20 |
| 2.5 | 60 | 150 | 39.65 | 2.51 | 41.68 | 11.57 | 95.41 |
| 2.5 | 120 | 140 | 43.52 | 2.23 | 40.28 | 10.68 | 96.71 |
| 2.5 | 120 | 170 | 0 | 25.92 | 46.83 | 16.53 | 89.28 |

For comparison, Table 6 summarizes the catalysis results for dehydrative cyclization of sorbitol to isosorbide using p-toluenesulfonic acid alone.

TABLE 6 p-TsOH

| Load (mol %) | Time (min) | Temp (° C.) | Sorbitol (wt. %) | Iso-sorbide (wt. %) | 1,4-sorbitan (wt. %) | 2,5-sorbitan(s) (wt. %) | Account-ability (%) |
|---|---|---|---|---|---|---|---|
| 0.1 | 180 | 130 | 32.23 | 2.68 | 51.32 | 9.14 | 95.37 |
| 0.1 | 120 | 140 | 17.05 | 6.92 | 63.22 | 6.22 | 93.41 |
| 0.1 | 60 | 150 | 22.62 | 7.13 | 59.24 | 2.69 | 91.68 |
| 0.5 | 180 | 130 | 0 | 26.65 | 50.32 | 10.59 | 87.56 |
| 0.5 | 120 | 140 | 0 | 35.51 | 37.75 | 10.04 | 83.30 |
| 0.5 | 60 | 150 | 0 | 42.20 | 28.29 | 11.06 | 81.55 |

For comparison, Table 7 summarizes the catalysis results for dehydrative cyclization of sorbitol to isosorbide using gallium trifluoromethanesulfonate alone.

TABLE 7

Ga(OTf)$_3$

| Load (mol %) | Time (min) | Temp (° C.) | Sorbitol (wt. %) | Iso-sorbide (wt. %) | 1,4-sorbitan (wt. %) | 2,5-sorbitan(s) (wt. %) | Account-ability (%) |
|---|---|---|---|---|---|---|---|
| 0.005 | 180 | 130 | 89.2 | 0 | 10.62 | 1.92 | 100.00 |
| 0.005 | 120 | 140 | 78.5 | 0.00 | 25.16 | 3.77 | 99.87 |
| 0.005 | 60 | 150 | 82.2 | 0.00 | 14.69 | 3.17 | 100.00 |
| 0.01 | 180 | 130 | 81.8 | 0.00 | 14.72 | 2.90 | 99.82 |
| 0.01 | 120 | 140 | 73.7 | 0.31 | 26.01 | 2.97 | 99.23 |
| 0.01 | 60 | 150 | 67.0 | 0.63 | 24.79 | 6.02 | 98.38 |
| 0.05 | 120 | 140 | 32.9 | 4.47 | 47.02 | 8.08 | 92.51 |
| 0.05 | 60 | 150 | 28.9 | 6.01 | 44.13 | 8.53 | 87.62 |

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently know or to be developed, which may be used within the scope of the invention. Therefore, unless changes otherwise depart from the scope of the invention, the changes should be construed as being included herein.

We claim:

1. A process for preparing a cyclic dehydration product comprising: contacting a sugar alcohol with a homogeneous mixed-acid catalyst reaction mixture containing a reducing Brønsted acid, having a pKa of about 1.0-1.5, in combination with a water-tolerant Lewis acid selected from the group consisting of: aluminum trifluoromethanesulfonate (Al (OTf)$_3$), gallium trifluoromethanesulfonate (Ga(OTf)$_3$, bismuth trifluoromethanesulfonate (Bi (OTf)$_3$), scandium trifluoromethanesulfonate (Sc(OTf)$_3$), indium trifluoromethanesulfonate (In(OTf)$_3$), tin triflate (Sn(OTf)$_2$), and hafnium triflate (Hf(OTf)$_4$) at a temperature for a sufficient time to dehydrate and ring close said sugar alcohol to a corresponding cyclic dehydration product of the sugar alcohol in a product mixture.

2. The process according to claim 1, wherein said sugar alcohol is at least one of: sorbitol, mannitol, iditol, xylitol, erythritol, and 1,2,5,6-hexanetetrol (HTO).

3. The process according to claim 1, wherein said reducing Brønsted acid is phosphonic acid ($H_3PO_3$).

4. The process according to claim 1, wherein a molar ratio of said reducing Brønsted acid to said water-tolerant Lewis acid is from about 1000:1 to about 5:1.

5. The process according to claim 1, wherein said temperature is greater than 130° C. to about 190° C.

6. The process according to claim 1, wherein said reducing Brønsted acid is present at a concentration of about 1.0 mol % to about 20 mol % relative to the sugar alcohol.

7. The process according to claim 1, wherein said Brønsted acid is present at a concentration of about 0.01 mol % to about 2.0 mol % relative to the sugar alcohol.

8. The process according to claim 1, wherein said Lewis acid is present at a concentration of about 0.005 mol % to about 0.5 mol % relative to the sugar alcohol.

* * * * *